(12) United States Patent
Ouazzani et al.

(10) Patent No.: US 7,432,087 B2
(45) Date of Patent: Oct. 7, 2008

(54) METHOD FOR PREPARING (2S, 3R, 4S)-4-HYDROXYISOLEUCINE AND ANALOGUES THEREOF

(75) Inventors: Jamal Ouazzani, Massy (FR); Pierre Potier, Paris (FR); Nobumichi-André Sasaki, Les Ulis (FR); Qian Wang, Gif-sur-Yvette (FR)

(73) Assignee: Centre National de la Recherche Scientifque, Paris (FR)

( * ) Notice: Subject to any disclaimer, the term of this patent is extended or adjusted under 35 U.S.C. 154(b) by 370 days.

(21) Appl. No.: 10/960,513

(22) Filed: Oct. 8, 2004

(65) Prior Publication Data

US 2005/0079587 A1    Apr. 14, 2005

Related U.S. Application Data

(62) Division of application No. 10/239,194, filed on Dec. 10, 2002, now abandoned.

(51) Int. Cl.
C12P 13/06    (2006.01)
C12P 13/04    (2006.01)

(52) U.S. Cl. ........................ 435/116; 435/106; 435/41
(58) Field of Classification Search .................. 435/116
See application file for complete search history.

(56) References Cited

FOREIGN PATENT DOCUMENTS

WO    WO 97/32577    9/1997

OTHER PUBLICATIONS

Kawai et al., 1994, Tetrahedron Letters, 35, 147-8 ☐☐.*
Anelli et al., 1987, J. Org. Chem., 52, 2559-62 ☐☐.*

Ishitani et al., Jan. 25, 2000, J. Am. Chem. Soc., 122, 762-6.*
XP 000610220; Alcock et al., Stereochemistry of the 4-Hydroxyisoleucine From Trigonella Foenum-Graecum; Phytochemistry, vol. 28. No. 7, pp. 1835-1841, 1989.
XP 002156490; Hasan et al., Die Vier Diastereomeren y-Hydroxyisoleucinlactone; Liebigs Ann. Chem. 1976; pp. 781-787 (Abstract Only).
XP 002156491; Gieren et al.; Die Konfiguration Der Hydroxylierten Isoleucine Der Amatoxine; Liebigs Ann. Chem.; 1974; pp. 1561-1569 (Abstract Only).
XP 002020594; Petit et al., PS 8 Insulin Secretion In Vitro (Abstract Only).
Kawai et al., Stereoselective Synthesis of Ethyl (2S, 3S)-Anti-2-Methyl-3-Hydroxybutanoate Mediated by an Oxidoreductase From Geotrichum Candidum, vol. 35, Issue 1, Jan. 3, 1994, pp. 147-148 (Abstract Only).
Zheng et al., Asymmetric Reduction of Ketoesters With Alcohol Dehydrogenase From Thermoanaerobacter Ethanolicus, Bioorganic & Medicinal Chemistry Letters, vol. 2 Issue 6, Jun. 1992, pp. 619-622 (Abstract Only).

* cited by examiner

*Primary Examiner*—Ruth A Davis
*Assistant Examiner*—Sheridan R Macauley
(74) *Attorney, Agent, or Firm*—Jacobson Holman PLLC

(57) ABSTRACT

The invention concerns a method for preparing a-amino acids of general formula (2S-1) wherein: the group R1 represents a hydrogen atom, a group protecting the amino group or a group of formula —COOR2 wherein the group R2 represents a C1-C6 alkyl group, an aryl or aralkyl group. The invention also concerns a-amino acids of general formula (2S-1) wherein the group R1 represents a group protecting the amino group or a group of formula —COOR2 wherein the group R2 represents a C1-C6 alkyl group, an aryl or aralkyl group and their use as medicine.

3 Claims, 4 Drawing Sheets

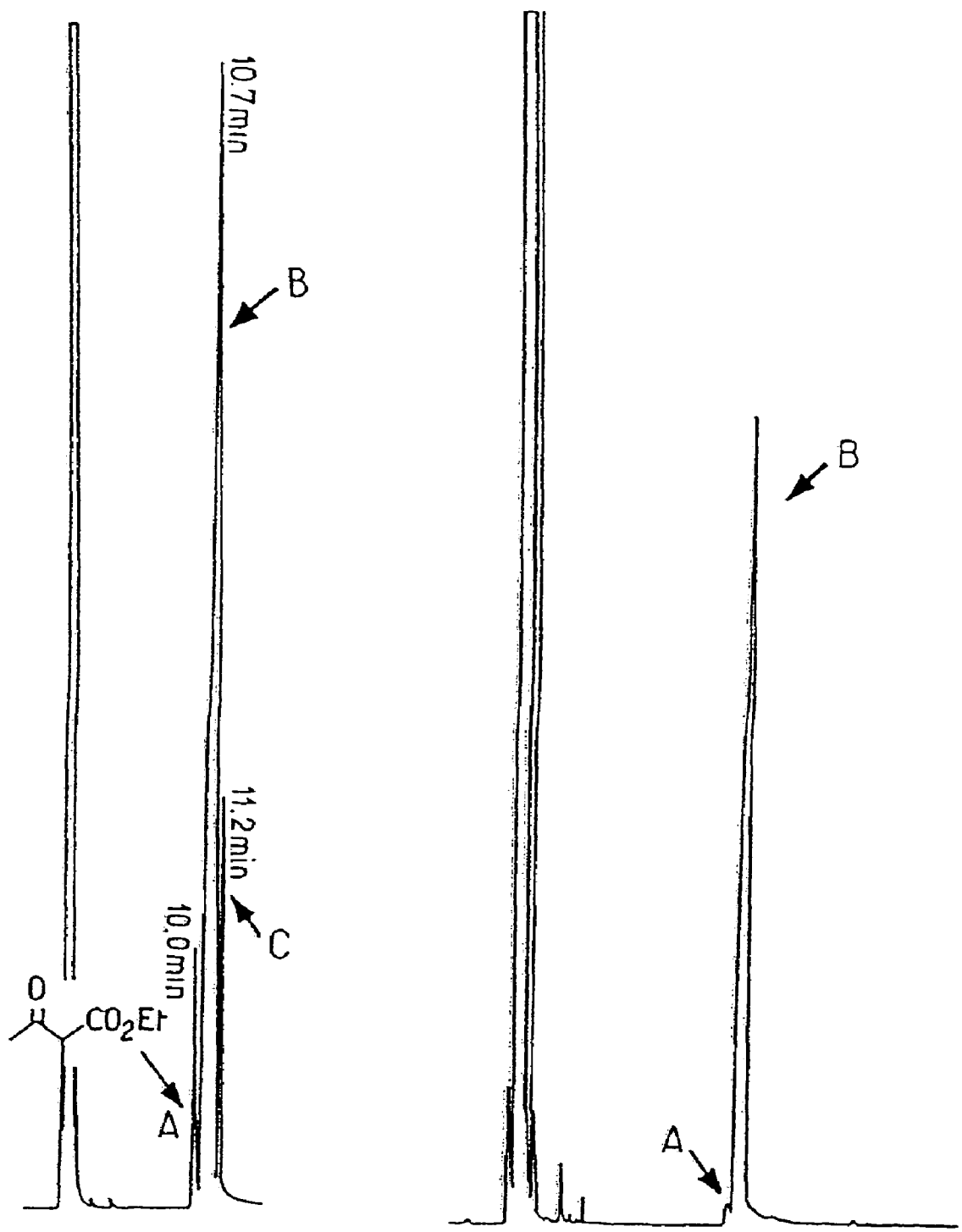
FIG_1a    FIG_1b

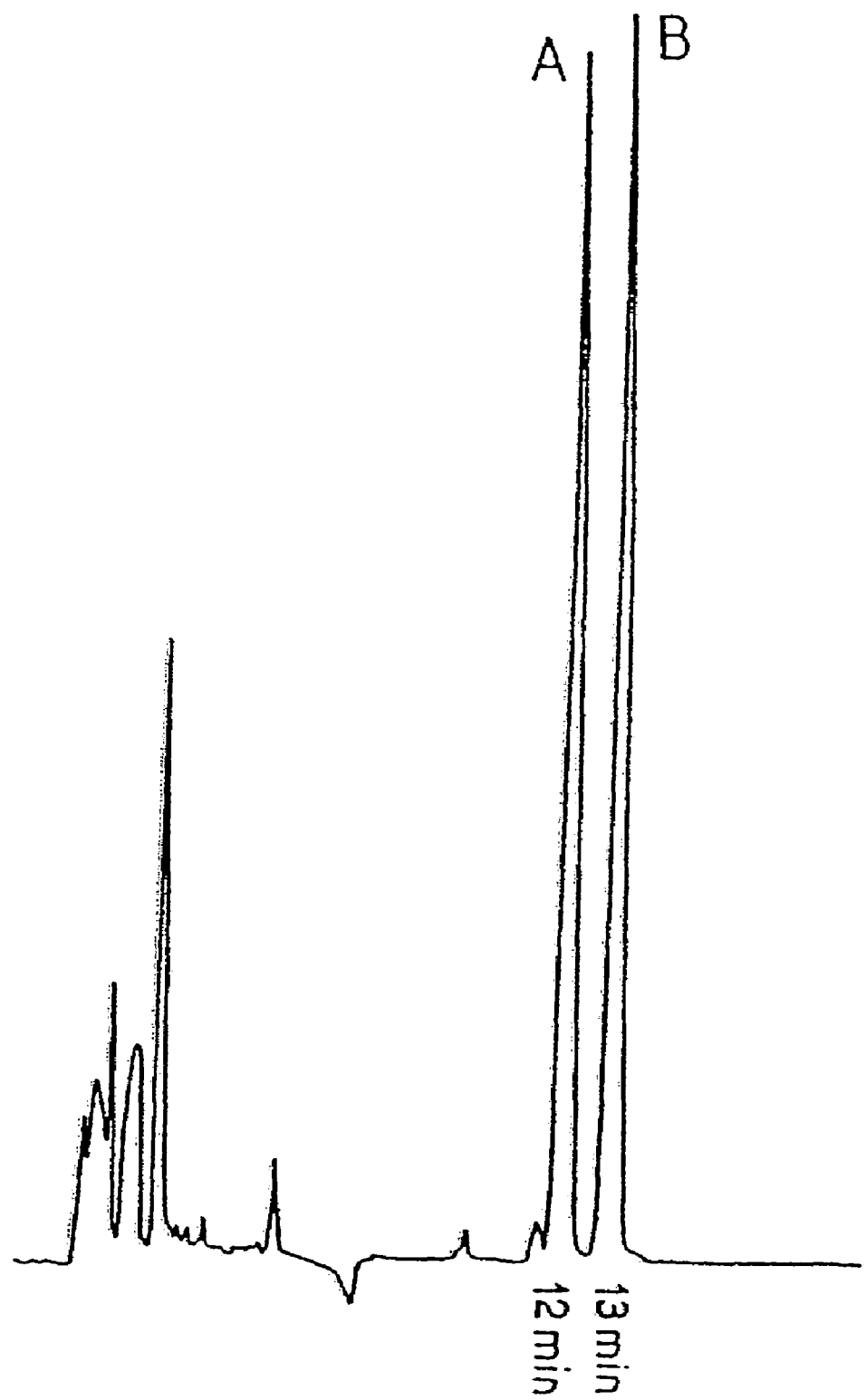
FIG_2a

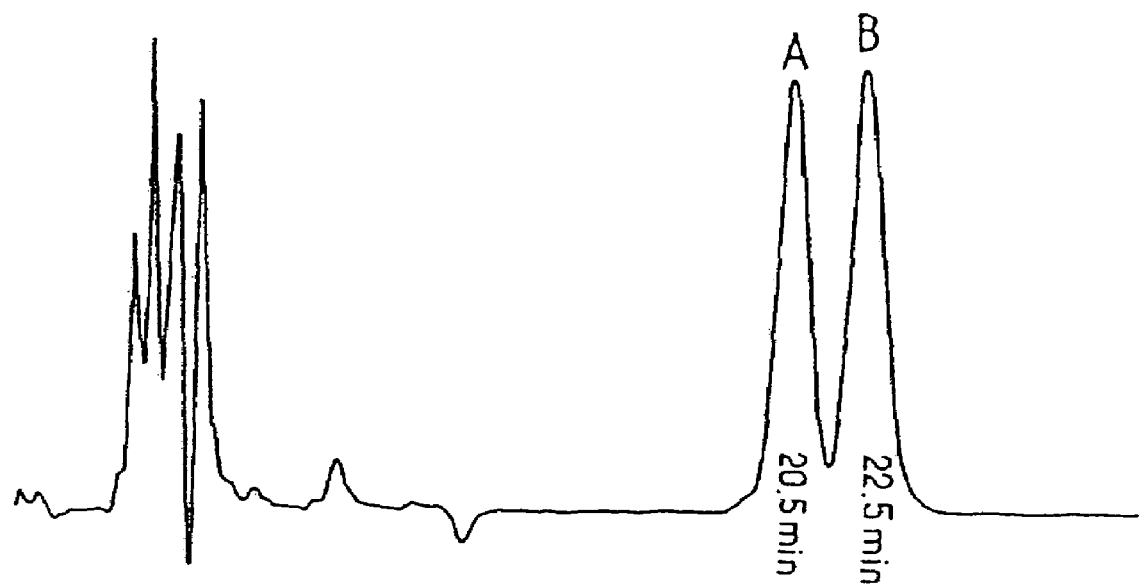
FIG_2b
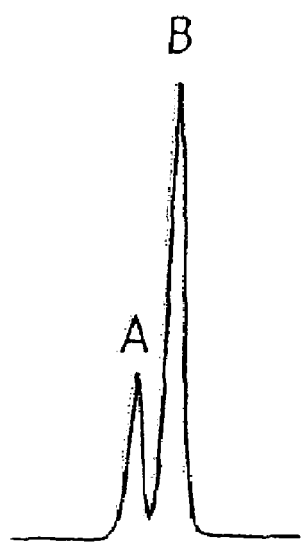
FIG_3a
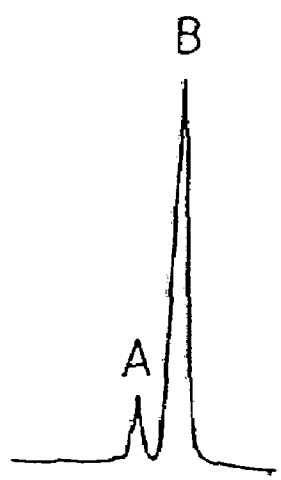
FIG_3b

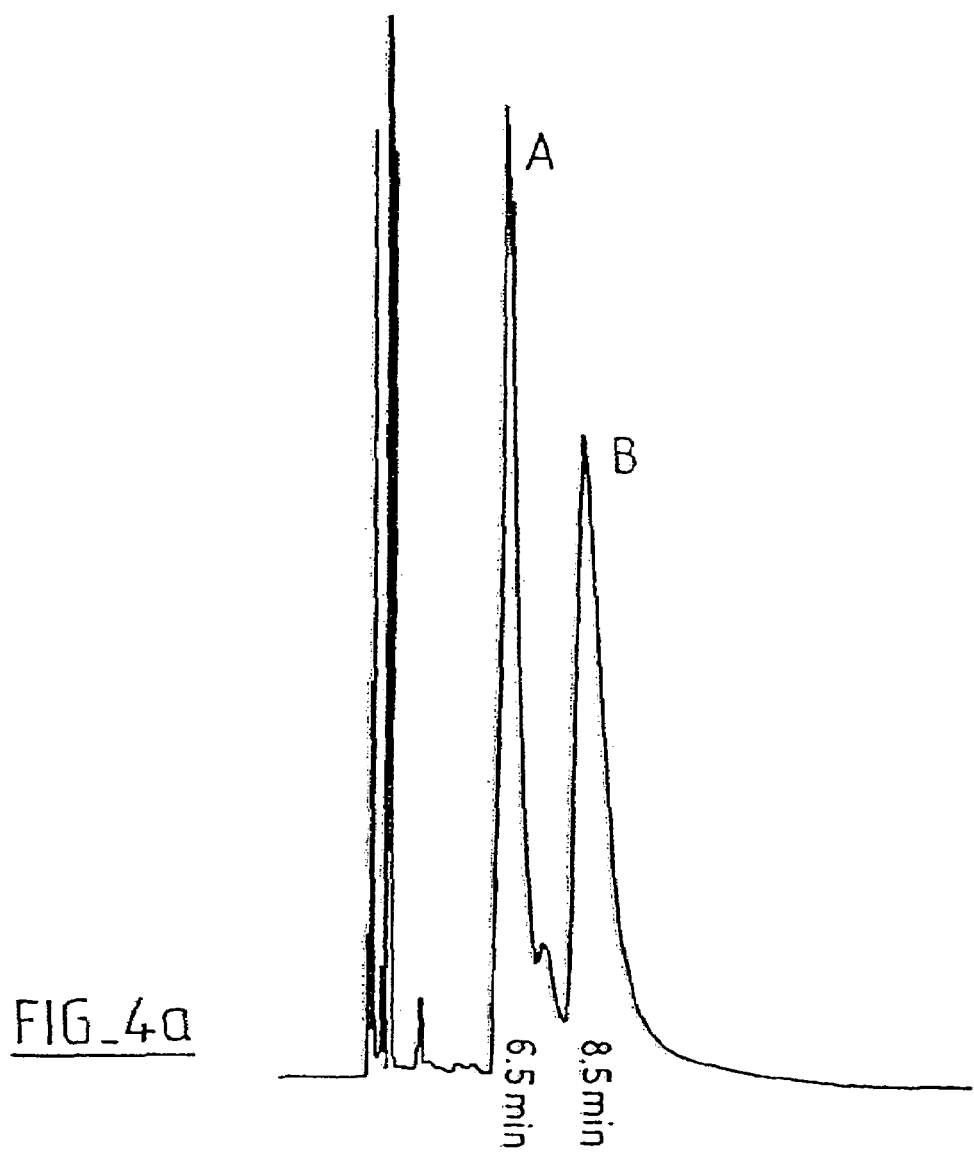
FIG_4a
6.5 min
8.5 min
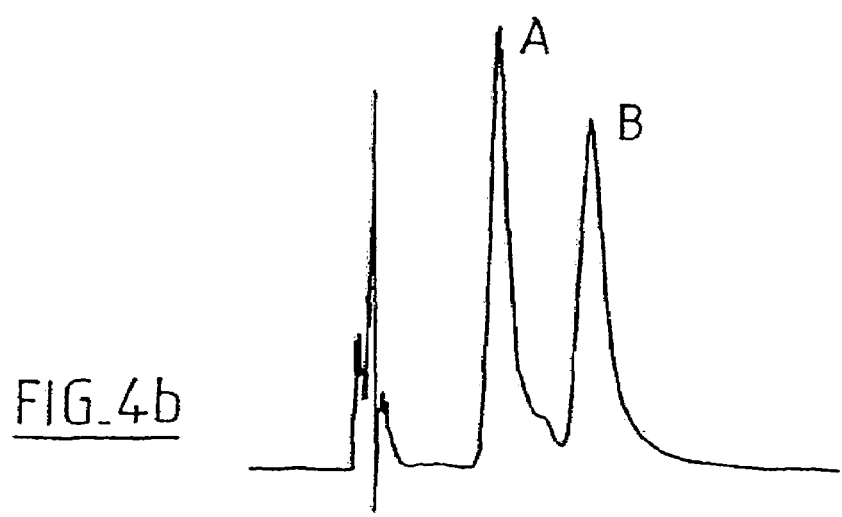
FIG_4b

METHOD FOR PREPARING (2S, 3R, 4S)-4-HYDROXYISOLEUCINE AND ANALOGUES THEREOF

This patent application is a divisional of patent application Ser. No. 10/239,194 filed Dec. 10, 2002, now abandoned and is incorporated by reference herein in its entirety.

The present invention relates to methods for preparing α-amino acids.

It relates in particular to a method for preparing an α-amino acid of the following general formula (2S)-I:

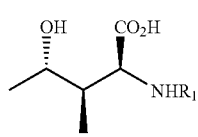

(2S)-I in which the group $R_1$ represents a hydrogen atom, a group protecting the amine group or a group of formula —$COOR_2$ in which the group $R_2$ represents a $C_1$-$C_6$ alkyl group, an aryl or aralkyl group.

It also relates to the α-amino acids of general formula (2S)-I in which the group $R_1$ represents a group protecting the amine group or a group of formula —$COOR_2$ in which the group $R_2$ represents a $C_1$-$C_6$ alkyl group, an aryl or aralkyl group and their use as medicine.

In 1973, Fowden et al. reported the presence of (2S,3R,4R)-4-hydroxy-3-methylpentanoic acid (4-hydroxy-isoleucin) 1 in fenugreek (*Trigonella foenumgraecum*) which is an annual herbaceous plant which is widespread in regions of Asia, Africa and Europe (Fowden et al. *Phytochemistry* 1973, 12, 1707-1711). Its absolute configuration was subsequently restudied and corrected as being (2S,3R,4S) by Alcock et al. in 1989 (*Phytochemistry* 1989, 28, 1835-1841). Thio α-amino acid of the following formula 1:

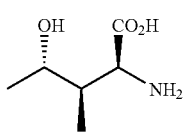

1 also proved to be a component of γ-amanitin, a deadly toxic cyclic peptide produced in *Amanita phalloide* (Wieland et al. *Liebigs Ann. Chem.* 1970, 736, 95-99; Gieren et al. *Liebigs Ann. Chem.* 1974, 1561-1569 and Hasan et al. *Liebigs Ann. Chem.* 1976, 781-787). It has been demonstrated that (2S,3R,4S)-4-hydroxyisoleucine 1 possesses an insulinotropic activity (Travis et al. in "*The Pharmacological Basis of Therapeutics*", Goodman L. S. and Gilman A. ed., 1970, p. 1581, MacMillan, London; Sauvaire et al. *Diabetes* 1998, 47, 206-210, Petit et al. *Diabetologia* 1995, 38, A101; Fernandez-Alvarez et al. *Diabetologia* 1996, 39, A234; Ribes et al. *Diabetologia* 1996, 39, A234; Petit et al. *Diabetologia* 1997, 40, A112; Broca et al. *Diabetologia*, 1998, 41, A239; Broca et al. *Diabetologia* 1999, 42, A 129 and international application PCT WO9732577). Despite this discovery that 1 as a novel medicine was of potential interest for the treatment of noninsulin-dependent diabetes mellitus only the asymmetric synthesis of the (2R,3R,4R) and (2S,3R,4R) diastereomers has been disclosed up until now (Inghardt et al. *Tetrahedron* 1991, 47, 6469-6482). 1 on the other hand is only obtained by extraction from fenugreek seeds which is a very laborious and expensive process (planting, maintenance, harvest, transport, extraction, and the like). In particular, the removal of glycine, the concomitant amino acid, is extremely difficult in the extraction process (Sauvaire et al. *Phytochemistry* 1984, 23, 479-486). Is reported that the overall yield of 1 from dried plant matter is 0.56% w/w (Sauvaire et al. *Diabetes* 1998, 47, 206-210). Consequently, there is still a need to have an easy and economic method for obtaining 1. Now, surprisingly, the asymmetric method of synthesis described in the present invention makes it possible to provide (2S,3R,4S)-4-hydroxyisoleucine 1 and its analogues of formula (2S)-1 in an industrial quantity and of an optically pure quality in an economically highly advantageous and very practical manner.

The α-amino acids of the following general formula (2S)-I:

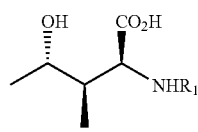

(2S)-I in which the group $R_1$ represents a group protecting the amine group or a group of formula —$COOR_2$ in which the group $R_2$ represents a $C_1$-$C_6$ alkyl group, an aryl or aralkyl group having never been synthesized are therefore novel and also form part of the invention.

The present invention therefore relates to a method for synthesizing compounds of general formula (2S)-I in which the group $R_1$ represents a hydrogen atom, a group protecting the amine group or a group of formula —$COOR_2$ in which the group $R_2$ represents a $C_1$-$C_6$ alkyl group, an aryl or aralkyl group.

The term "group protecting the amine group" is understood to mean, for the purposes of the present invention, any $C_1$-$C_6$ alkyl group, any aryl or aralkyl group and in particular any labile group protecting the amine functional group and well known to persons skilled in the art, in particular of the benzyl, (S)-(+)-p-toluenesulfino

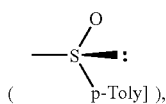

( p-Toly] ), (S)-1-phenylethyl (—$CH(CH_3)Ph$) and (S)-1-phenyl-2-hydroxyethyl (—$CH(CH_2OH)Ph$) type.

The term "$C_1$-$C_6$ alkyl group" is understood to mean, for the purposes of the present invention, any substituted or unsubstituted, linear or branched $C_1$-$C_6$ alkyl group, in particular the methyl, ethyl or t-butyl groups.

The term "aryl group" is understood to mean, for the purposes of the present invention, one or more aromatic rings having 5 to 8 carbon atoms, which may be condensed or fused, substituted or unsubstituted. In particular, the aryl groups may be phenyl or naphthyl groups.

The term "aralkyl group" is understood to mean, for the purposes of the present invention, aryl groups as defined above, linked via an alkyl group as defined above. In particular, an aralkyl group is a benzyl group.

This method comprises in particular the steps of:

a) diastereo- and enantioselective reduction of the ethyl 2-methylacetoacetate of the following formula 2:

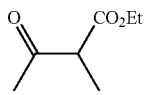

2 in order to obtain the compound of the following formula 3:

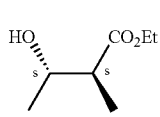

3 with an enantiomeric excess (ee) of at least about 85%, advantageously of at least about 90%, and a diastereomeric excess (de) of at least about 90%, advantageously of at least about 95%. The de is determined by gas chromatography (GC) analysis and the ee is estimated by the $^1$H and $^{13}$C NMR spectra of the ethyl (S)-lactate of 3.

Advantageously, the diastereo- and enantioselective reduction is carried out using an enzyme, still more advantageously using a microorganism containing this enzyme, in particular *Geotrichum candidum* (Buisson et al. *Tetrahedron Lett.* 1987, 28, 3939-3940 and Kawai et al. *Tetrahedron Lett.* 1994, 35, 147-148).

The enzyme used may be isolated in particular from *Geotrichum candidum* (deposited at the Collection Nationale de Culture de Microorganismes on 8 Dec. 1999 with the registration number: I-2366) and used in powdered form or attached to a support.

b) protection of the OH group of the alcohol of formula 3 with a group Y. For the purposes of the present invention, the expression "group protecting the OH group" is understood to mean any group known as such by persons skilled in the art, in particular the benzyl (Bn), t-butyl or tetrahydropyran (THP) groups.

c) reduction to an alcohol of the —COOEt group of the compound obtained in b). The reduction may be carried out by any method well known to persons skilled in the art, in particular using LiAlH$_4$ or diisobutylaluminum hydride (DIBAL).

d) oxidation of the unprotected OH group obtained in c) to give the aldehyde of the following general formula II:

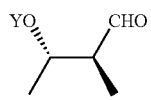

II in which the group Y represents a group protecting the OH group.

The oxidation may be carried out by any method well known to persons skilled in the art and in particular by treating with a pyridine/sulfur trioxide (Py.SO$_3$) complex in dimethyl sulfoxide (DMSO), by Swern oxidation or by treating with 2,2,6,6-tetramethyl-1-piperidinyloxy containing a free radical (TEMPO) using NaOCl as reducing agent in the presence of NaBr/NaHCO$_3$/H$_2$O.

From the compound of general formula II, two routes of synthesis of the compounds of general formula (2S)-I are possible:

The first route of synthesis (method A) is an asymmetric approach and comprises the following steps e$_1$) to h$_1$):

e$_1$) treatment of the compound of general formula II with a sulfinamide having the configuration (S)(+) in order to obtain the compound of the following general formula IV:

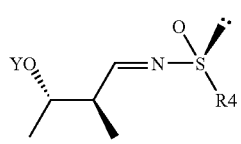

IV in which the group Y represents a group protecting the OH group and the group R4 represents a C$_1$-C$_6$ alkyl, aryl or aralkyl group.

The sulfinamides having the configuration (S) (+) which may be used are in particular those for which the group R4 represents the t-butyl, 2-methoxy-1-naphthalenyl, 2-[1-(t-butylcarbonylamino)ethyl]benzyl or p-toluene group.

(S)-(+)-p-toluenesulfinamide may be easily prepared from (1R,2S,5R)-(−)-menthyl-(S)-p-toluenesulfinate and from lithium 1,1,1,3,3,3-hexamethyldisiloxane (LiHMDS).

f$_1$) treatment of the compound of general formula IV, in particular with ethylisopropyloxyaluminum cyanide (EtAl (OiPr)CN), in order to obtain the aminonitrile of the following general formula V:

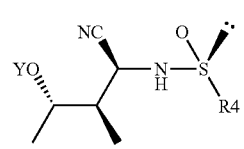

V in which the group Y represents a group protecting the OH group and the group R4 represents a C$_1$-C$_6$ alkyl, aryl or aralkyl group g$_1$) treatment with an acid, in particular by refluxing in an inorganic acid of the HCl or HBr type, of the aminonitrile of general formula V in order to obtain the salt of the lactone of the following formula 9:

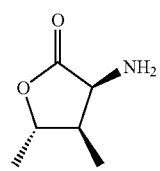

9

The expression lactone salt is understood to mean the salts obtained following the treatment with the inorganic acid, in particular chlorides or bromides. It is also possible, by another variant method, to obtain aminonitriles in step $f_1$) and lactones in step $g_1$) of good configurations by an asymmetric synthesis using chiral amines for the asymmetric induction at the $C_2$ position of the compounds of general formula II. These methods are well known to persons skilled in the art and use in particular, as chiral amines, (S)-α-methybenzylamine, (S)-α-phenyl-glycinol, (S)-α-N-benzylphenylglycinol, (S)-α-butyl-benzylamine, (S)-α-ethylbenzylamine, (S)-α-naphthyl-benzylamine, (4S,5S)-(+)-5-amino-2,2-dimethyl-4-phenyl-1,3-dioxane or 2,3,4,6-tetra-O-pivaloyl-β-D-galactopyranosylamine.

$h_1$) alkaline hydrolysis, in particular with LiOH, of the salt of the lactone of formula 9 in order to obtain the compound of general formula (2S)-I in which the group $R_1$ represents a hydrogen atom. This compound may be purified, if necessary, by ion-exchange resin Dowex 50WX8 (H+ form), by neutralizing with an organic acid, in particular formic acid or acetic acid, and crystallization from an alcohol, in particular from isopropanol, propanol or ethanol, or by any other method known to persons skilled in the art.

As a variant, the second route of synthesis (method B) from the compound of general formula II comprises the following steps $e_2$) to $h_2$):

$e_2$) treatment of the compound of general formula II in order to obtain the aminonitrile of the following general formula III:

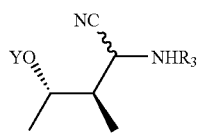

III in which:

the group Y represents a group protecting the OH group and the group $R_3$ represents a group protecting the amine group.

In particular, to obtain the compound of general formula III in which the group $R_3$ represents the benzyl group (Bn), the compound of general formula II is preferably treated with benzylamine hydrochloride and KCN, preferably in an equimolar quantity, or still more preferably with benzylamine and trimethylsilyl cyanide (TMSCN). The aminonitrile obtained is a racemic mixture of diastereomers (1S) and (1R), in particular with an (1S):(1R) ratio of 55:45.

Preferably, to obtain the compound of general formula III in which the group $R_3$ represents the group (—CH(CH$_3$)Ph), it is possible to treat the compound of general formula II preferably with (S)—NH$_2$CH(CH$_3$)Ph and TMSCN or the salt of (S)—NH$_2$CH(CH$_3$)Ph and KCN. The aminonitrile obtained is a mixture of diastereomers with in particular a (1S):(1R) ratio of 3.5:1 to 4:1.

$f_2$) treatment with an acid, in particular by refluxing in an inorganic acid of the HCl or HBr type, of the aminonitrile of general formula III in order to obtain the lactone of the following general formula VI:

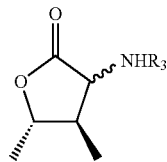

VI in which the group $R_3$ represents a hydrogen atom or a group protecting the amine group. The yield of this reaction is quantitative.

Step $f_2$) may be followed by an additional step $f_{2.1}$) of treatment of the lactone of general formula VI in order to obtain the lactone of the following general formula VII:

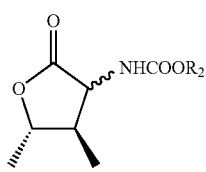

VII in which the group $R_2$ represents a $C_1$-$C_6$ alkyl group, an aryl or aralkyl group.

This treatment of the lactone of general formula VI is carried out in a known manner by persons skilled in the art and in particular using hydrogen in the presence of a catalyst, advantageously containing palladium and still more advantageously with the Pd—C catalyst, and a compound A containing a group —COOR$_2$ in which the group $R_2$ represents a $C_1$-$C_6$ alkyl group, and aryl or aralkyl group. Advantageously, in the case where it is desired to prepare a compound of formula VII in which the group $R_2$ represents a methyl group, the compound A is (COOCH$_3$)$_2$O, in that where the group $R_2$ represents a t-butyl group, the compound A is di-tert-butyl bicarbonate and in that where the group $R_2$ represents the benzyl group, the compound A is benzyloxycarbonyl chloride.

$g_2$) diastereoselective hydrolysis of the lactone of general formula VI or VII in order to obtain the compound of general formula (2S)-I.

This step $g_2$) may in particular consist of three variants.

The first variant $g_{2.1}$) relates only to the lactones of general formula VII or the lactones of general formula VI in which the group $R_3$ represents a group protecting an amine group. It then consists in the steps $g_{2.1.1}$) to $g_{2.1.3}$):

$g_{2.1.1}$) alkaline hydrolysis, in particular with LiOH hydrate in water, of the lactone in order to obtain a mixture of diastereomers of the following general formula I:

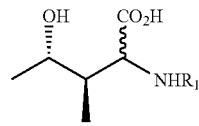

I in which the group $R_1$ represents a group protecting the amine group or a group of formula —COOR$_2$ in which the group $R_2$ represents a $C_1$-$C_6$ alkyl group, an aryl or aralkyl group. This mixture preferably comprises a 7:3 ratio in favor of the (2S) isomer. This hydrolysis may be monitored by thin-layer chromatography (TLC) until it is complete and can be carried out, with stirring, for 1 hour at room temperature.

$g_{2.1.2}$) the addition of an organic acid, preferably trifluoroacetic acid (TFA), in the form of traces, preferably 2% v/v, and heating, preferably to a temperature of between about 40 and about 80° C., still more preferably between about 50 and about 60° C., in order to recyclize the compound of the following general formula (2R)-I:

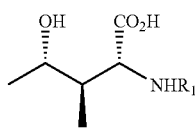

(2R)-I in which the group $R_1$ represents a group protecting the amine group or a group of formula —$COOR_2$ in which the group $R_2$ represents a $C_1$-$C_6$ alkyl group, an aryl or aralkyl group, into a lactone of the following general formula (3R)-VIII:

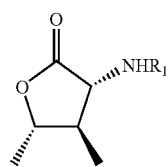

(3R)-VIII in which the group $R_1$ represents a group protecting the amine group or a group of formula —$COOR_2$ in which the group $R_2$ represents a $C_1$-$C_6$ alkyl group, an aryl or aralkyl group. The recyclization may be monitored by high-performance liquid chromatography (HPLC).

$g_{2.1.3}$) the extraction, with an organic solvent, in particular with ethyl acetate (EtOAc) and still more particularly with an EtOAc/heptane mixture in a 1:1 ratio, of the lactone of general formula (3R)-VIII in order to recover the compound of general formula (2S)-I in which the group $R_1$ represents a group protecting the amine group or a group of formula —$COOR_2$ in which the group $R_2$ represents a $C_1$-$C_6$ alkyl group, an aryl or aralkyl group.

The second variant $g_{2.2}$) consists in the steps $g_{2.2.1}$) to $g_{2.2.3}$)

$g_{2.2.1}$) the diastereoselective enzymatic hydro-lysis of the lactone of general formula (3R)-VI or (3R)-VII by hydrolases to give the compound of general formula (2R)-I. These hydrolases may be used in purified, or partially purified form or produced in situ by microorganisms.

In particular, it is possible to use crude enzymatic preparations or live microbial cells. Advantageously, a pig liver acetone powder, marketed by the company Sigma under the reference L.8251, or the microbial strain *Penicillium* (deposited on 29 Sep. 1998 at the Collection Nationale de Cultures de Microorganismes with the registration number: I-2081) is used to carry out this hydrolysis.

$g_{2.2.2}$) the extraction with an organic solvent, preferably EtOAc, of the remaining nonhydrolyzed lactone of the following general formula (3S)-VIII:

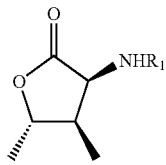

(3S)-VIII in which the group $R_1$ represents a hydrogen atom, a group protecting the amine group or a group of formula —$COOR_2$ in which the group $R_2$ represents a $C_1$-$C_6$ alkyl group, an aryl or aralkyl group, $g_{2.2.3}$) the nonselective enzymatic hydrolysis of the lactone of general formula (3S)-VIII in order to obtain the compound of general formula (2S)-I in which the group $R_1$ represents a hydrogen atom, a group protecting the amine group or a group of formula —$COOR_2$ in which the group $R_2$ represents a $C_1$-$C_6$ alkyl group, an aryl or aralkyl group.

Step $g_2$) may be followed by an additional step $h_2$) in the case where the group $R_1$ of the compound of general formula (2S)-1 represents a group protecting the amine group or a group of formula —$COOR_2$ in which the group $R_2$ represents a $C_1$-$C_6$ alkyl group, an aryl or aralkyl group allowing the production of (2S,3R,4S)-4-hydroxyisoleucine 1. This additional step consists in a catalytic hydrogenolysis, in particular using a palladium-based catalyst, still more particularly using the Pd/C catalyst, of the compound of formula (2S)-I in which the group $R_1$ represents a group protecting the amine group or a group of formula —$COOR_2$ in which the group $R_2$ represents a $C_1$-$C_6$ alkyl group, an aryl or aralkyl group.

The third variant $g_{2.3}$) relates only to the lactones of general formula VI in which the group $R_3$ represents a group protecting the amine group, in particular a group (—$CH(CH_3)Ph$). It then consists of the steps $g_{2.3.1}$) to 2.3.3):

$g_{2.3.1}$) crystallization from an organic solvent, advantageously isopropanol, of the lactone of general formula VI in which the group $R_3$ represents a group protecting the amine group so as to obtain the salt of the compound of formula (3S)-VIII in which the group $R_1$ represents a group protecting the amine group, $g_{2.3.2}$) catalytic hydrogenolysis, in particular using a palladium-based catalyst, still more particularly using the Pd/C catalyst, of the salt of the compound of formula (3S)-VIII in which the group $R_1$ represents a group protecting the amine group so as to obtain the salt of the lactone of formula 9, $g_{2.3.3}$) alkaline hydrolysis, in particular with LiOH, of the salt of the lactone of formula 9 in order to obtain the compound of general formula (2S)-I in which the group $R_1$ represents a hydrogen atom. This compound may be purified, if necessary, using an ion-exchange resin, in particular Dowex 50WX8 (H+ form), by neutralizing with an organic acid, in particular formic acid or acetic acid, and crystallization from an alcohol, in particular from isopropanol, propanol or ethanol, or by any other method known to persons skilled in the art.

The method according to the invention may be illustrated as a guide and without limitation by the following reaction scheme for the synthesis of (2S,3R,4S)-4-hydroxyisoleucine 1:

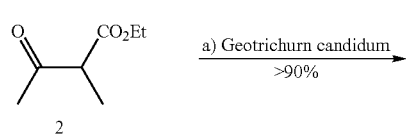
2
a) Geotrichum candidum
>90%
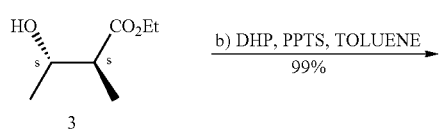
3
b) DHP, PPTS, TOLUENE
99%
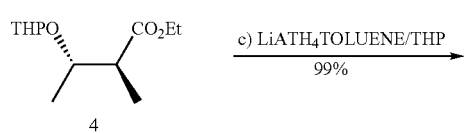
4
c) LiAlH₄ TOLUENE/THF
99%
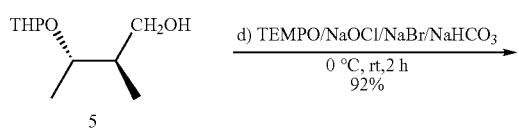
5
d) TEMPO/NaOCl/NaBr/NaHCO₃
0 °C, rt, 2 h
92%
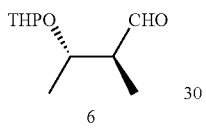
6
Method A
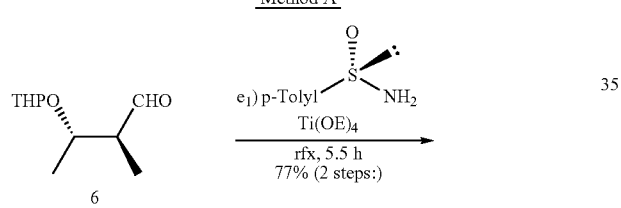
6
e₁) p-Tolyl-S(O)-NH₂
Ti(OEt)₄
rfx, 5.5 h
77% (2 steps:)
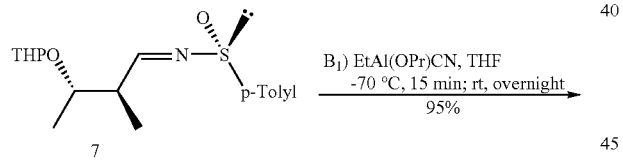
7
B₁) EtAl(OiPr)CN, THF
−70 °C, 15 min; rt, overnight
95%
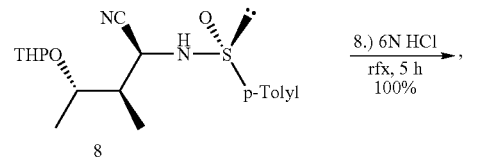
8
8.) 6N HCl
rfx, 5 h
100%
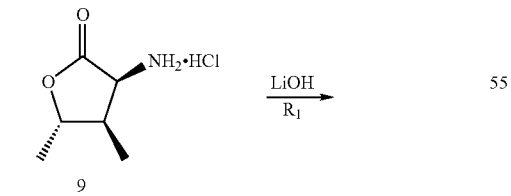
9
LiOH
R₁
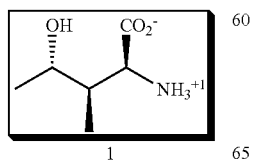
1
-continued
Method B
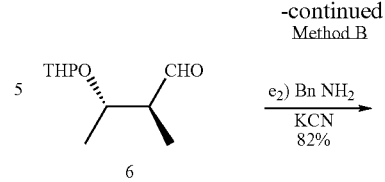
6
e₂) BnNH₂
KCN
82%
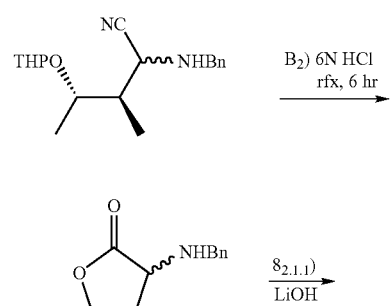
B₂) 6N HCl
rfx, 6 hr
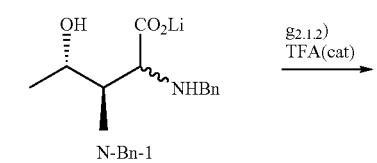
11
8₂.₁.₁)
LiOH
N-Bn-1
g₂.₁.₂)
TFA(cat)
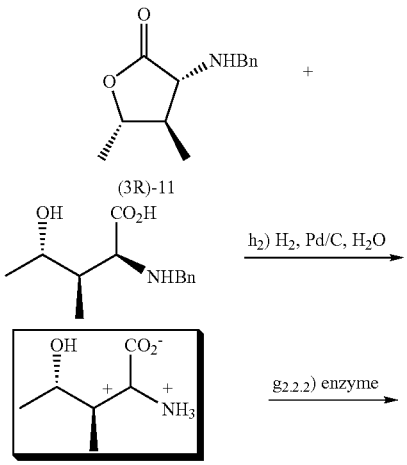
(3R)-11
h₂) H₂, Pd/C, H₂O
g₂.₂.₂) enzyme
1
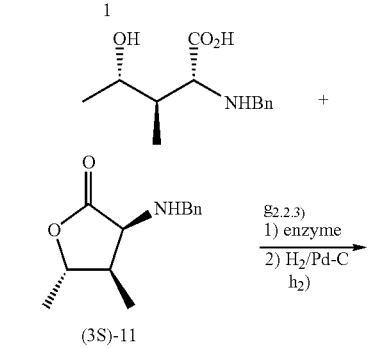
(3S)-11
g₂.₂.₃)
1) enzyme
2) H₂/Pd-C
h₂)

As a variant, the method B of synthesis of (2S,3R,4S)-4-hydroxyisoleucine 1 may have the following reaction scheme:
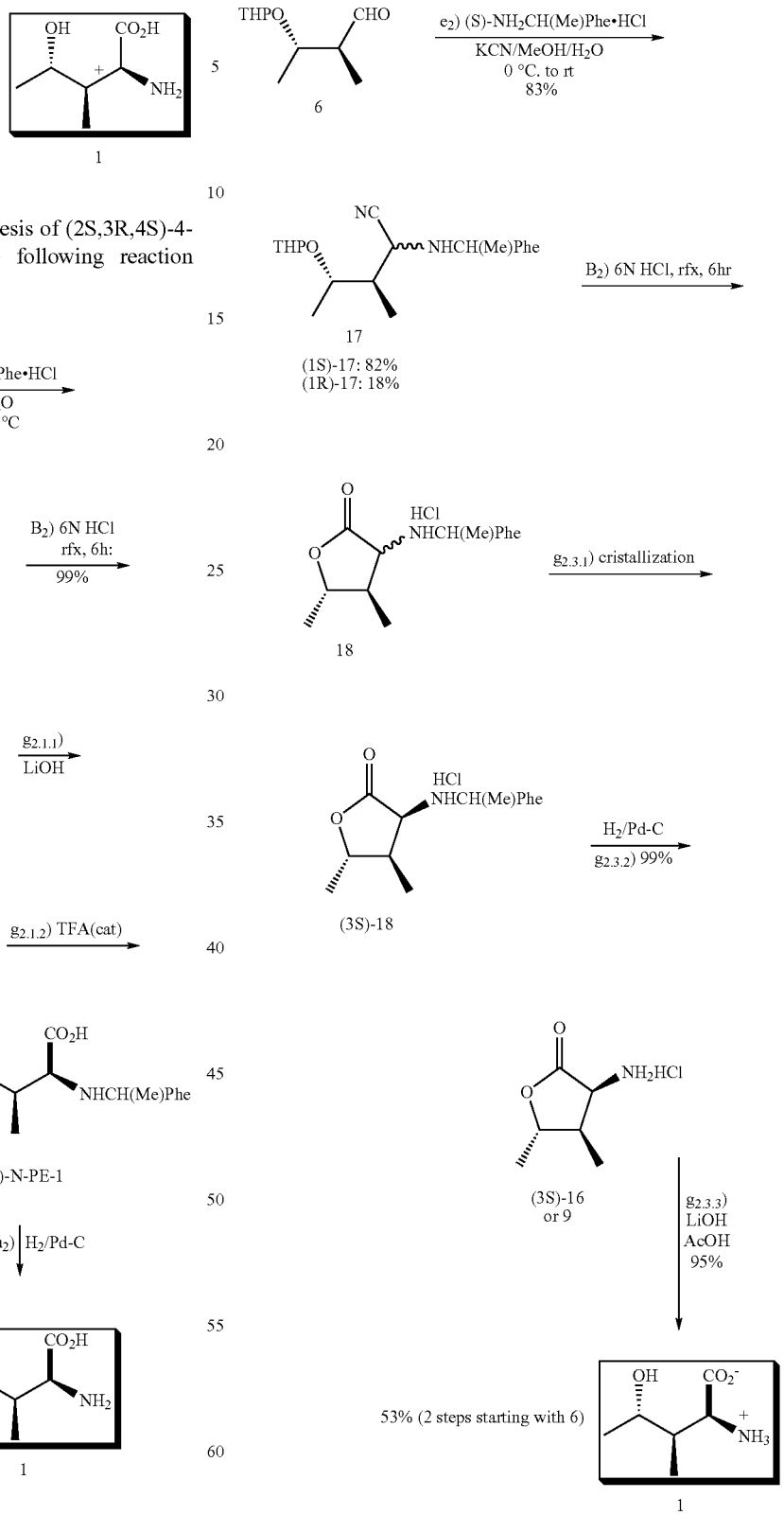
As a variant, the method B of synthesis of (2S,3R,4S)-4-hydroxyisoleucine 1 may also have the following reaction scheme:
The present invention also relates to the synthesis intermediates. The latter are in particular lactones of the following general formula VIII:

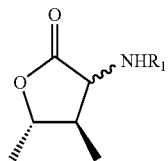

VIII in which the group $R_1$ represents a group of formula —$COOR_2$ in which the group $R_2$ represents a $C_1$-$C_6$ alkyl group, an aryl or aralkyl group. These compounds may be present in free form or in the form of salts of acids, in particular inorganic acids of the HCl or HBr type. They may also be present in the form of a mixture, in particular a racemic mixture, of diastereomers (3S) and (3R) or in their optically pure form (3S) or (3R). In particular, in the case where the group $R_1$ represents the group —$CH(CH_3)Ph$, these compounds may be present in the form of a mixture of diastereomers with a (3S)/(SR) ratio of 4:1.

The present invention also relates to the aminonitriles of the following general formula III:

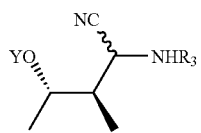

III in which:

the group Y represents a group protecting the OH group and the group $R_3$ represents a group protecting the amine group.

They may be present in the form of a mixture, in particular a racemic mixture, of the diastereomers (2S) and (2R) or in their optically pure (2S) or (2R) form. In particular, in the case where the group $R_3$ represents the group —$CH(CH_3)Ph$, these compounds may be present in the form of a mixture of diastereomers with a (2S)/(2R) ratio of 4:1.

In particular, the aminonitriles according to the present invention may be represented by the following general formula V:

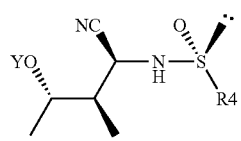

V in which:

the group Y represents a group protecting the OH group and the group R4 represents a $C_1$-$C_6$ alkyl, aryl or aralkyl group.

The present invention also relates to the compounds of the following general formula IV:

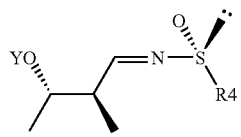

IV in which:

the group Y represents a group protecting the OH group and the group R4 represents a $C_1$-$C_6$ alkyl, aryl or aralkyl group.

The present invention also relates to the compounds of the following general formula I:

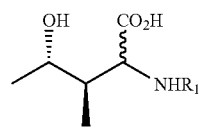

I in which the group $R_1$ represents a group of formula —$COOR_2$ in which the group $R_2$ represents a $C_1$-$C_6$ alkyl group, an aryl or aralkyl group. They may be present in the form of a mixture, in particular a racemic mixture, of the diastereomers (2S) and (2R) or in their optically pure (2S) or (2R) form. In particular, in the case where the group $R_1$ represents the group —$CH(CH_3)Ph$, these compounds may be present in the form of a mixture of diastereomers with a (2S)/(2R) ratio of 4:1.

The present invention also relates to the compounds of general formula (2S)-I in which the group $R_1$ represents a group protecting the amine group or a group of formula —$COOR_2$ in which the group $R_2$ represents a $C_1$-$C_6$ alkyl group, an aryl or aralkyl group as a medicine, in particular intended for the treatment of noninsulin-dependent diabetes mellitus or as an insulinotropic agent and its use for the manufacture of a medicine, in particular for the treatment of noninsulin-dependent diabetes mellitus.

The present invention also relates to the pharmaceutical compositions comprising, as active ingredient, a compound of general formula (2S)-I in which the group $R_1$ represents a group protecting the amine group or a group of formula —$COOR_2$ in which the group $R_2$ represents a $C_1$-$C_6$ alkyl group, an aryl or aralkyl group and an appropriate excipient. These compositions may be formulated for administration to mammals, including humans. The dosage may vary according to the treatment and according to the condition in question. These compositions are produced so that they can be administered by the digestive or parenteral route.

In the pharmaceutical compositions of the present invention for oral, sublingual, subcutaneous, intramuscular, intravenous, transdermal, local or rectal administration, the active ingredient may be administered in unit forms for administration, mixed with conventional pharmaceutical carriers, to animals or to human beings. The appropriate unit forms for administration comprise the forms for oral administration such as tablets, gelatin capsules, powders, granules and oral solutions or suspensions, the forms for sublingual or buccal administration, the forms for subcutaneous, intramuscular, intravenous, intranasal or intraocular administration and the forms for rectal administration.

When a solid composition in the form of tablets is prepared, the main active ingredient is mixed with a pharmaceutical vehicle such as gelatin, starch, lactose, magnesium stearate, talc, gum arabic and the like. It is possible to coat the tablets with sucrose or other appropriate substances or alternatively it is possible to treat them such that they have a prolonged or delayed activity and they continuously release a predetermined quantity of active ingredient.

A preparation in the form of gelatin capsules is obtained by mixing the active ingredient with a diluent and pouring the mixture obtained into soft or hard gelatin capsules.

A preparation in syrup or elixir form may contain the active ingredient together with a sweetener, an antiseptic, as well as a taste enhancer and an appropriate coloring.

The water-dispersible powders or granules may contain the active ingredient in the form of a mixture with dispersing agents or wetting agents, or suspending agents, and with flavor correctors or sweeteners.

DESCRIPTION OF THE FIGURES

FIG. 1 represents the GC analysis of the mixture obtained after incubating compound 2 with *Geotrichum candidum*. The carrier gas is helium with a pressure of 65 Kpa. The column used is DB.5 with the dimensions 30 m×0.32 mm. The detection is carried out using a flame ionization detector (FID) with an isotherm at 60° C. This analysis makes it possible to determine the percentage conversion of compound 2 to compound 3 and the diastereomeric excess. A, B and C correspond to compound 2, to compound 3 and to ethyl (2R,3S)-2-methyl-3-hydroxybutanoate respectively.

FIG. 1a represents the GC analysis of the mixture after 30 hours of incubation of compound 2 with *Geotrichum candidum*.

FIG. 1b represents the GC analysis of the mixture obtained after 48 hours of incubation of compound 2 with *Geotrichum candidum*.

FIG. 2 represents the HPLC analyses during the enzymatic hydrolysis of the lactone 11. A and B correspond to (3R)-(11) and (3S)-(11), respectively. The solvent used is a mixture of 35% acetonitrile and 0.2% triethylamine in water. The detection is carried out by UV at 250 nm.

FIG. 2a represents the analytical HPLC analysis. The column used is a $C_{18}$ hypersil ODS having the dimensions 5 µm, 250×4.6 mm. The flow rate is 1 ml/min.

FIG. 2b represents the preparative HPLC analysis. The column used is prep nova-pak.HR $C_{18}$ having the dimensions 6 µm 60 A 10×2.5 cm. The flow rate is 6 ml/min.

FIG. 3a represents a resolution obtained with a pig pancreas acetone powder after 48 hours of incubation. A and B correspond to (3R)-(11) and to (3S)-(11), respectively.

FIG. 3b represents a resolution obtained with a *penicillum* microbial strain after 48 hours of incubation. A and B correspond to (3R)-(11) and (3S)-(11), respectively.

FIG. 4 represents the HPLC analyses of the mixture of diastereomers of formula N-Bn-1 during the treatment with TFA. A and B correspond to (2S)-N-Bn-1 and to (2R)-N-Bn-1, respectively. The solvent used is a mixture of 20% acetonitrile and 0.1% TFA in water. The detection is carried out by UV at 250 nm.

FIG. 4a represents the analytical HPLC analysis at t=0 hour. The column used is a $C_{18}$ hypersil ODS having the dimensions 5 µm, 250×4.6 mm. The flow rate is 1 ml/min.

FIG. 4b represents the preparative HPLC analysis. The column used is prep nova-pak.HR $C_{18}$ having the dimensions 6 µm 60 A 10×2.5 cm. The flow rate is 6 ml/min.

The following examples of methods of preparation illustrate the invention without limitation.

Ethyl (2S,3S)-2-methyl-3-hydroxybutanoate (3)

The strain *Geotrichum candidum* LCM is cultured in a sterile medium containing (per liter of distilled water): $KH_2PO_4$ 1 g, $K_2HPO_4$ 2 g, $MgSO_4$ 0.5 g, $FeSO_4$ 20 mg, KCl 0.5 g, $NaNO_3$ 3 g, glucose 30 g, soluble corn extract 10 g. The culture (6 liters) was placed in a rotary stirrer for 3 days (200 rpm, 27° C.). After growth, the mycelium was recovered by filtration, resuspended in distilled water (2 liters) and shaken for a further 24 hours (200 rpm, 27° C.). The mycelium was filtered and was introduced into the reaction medium (2 liters) containing ethyl 2-methylacetate (2) (10 to 20 g/l), glucose at 1.5% and NaCl at 1% (% relative to the substrate). The mixture was shaken (200 rpm, 27° C.), 1 ml samples were collected and they were analyzed from time to time by GC in order to determine the percentage conversion and the diastereomeric excess (de) (FIG. 1a: after 30 hours). When the reaction was complete (after about 48 h: FIG. 1b), the medium was extracted with ethyl acetate in order to obtain ethyl (2S,3S)-2-methyl-3-hydroxybutanoate (3) with a yield of 90 to 95%: $[\alpha]_D$=+26° (c 3.0; $CHCl_3$); $^1H$ NMR (250 MHz, $CDCl_3$) δ 4.18 (q, J=7.1 Hz, 2H); 3.89 (quintuplet, J=6.5 Hz, 1H); 2.64 (broad s, 1H); 2.44 (quintuplet, J=7.2 Hz, 1H); 1.28 (t, J=7.1 Hz, 3H); 1.22 (d, J=6.4 Hz, 3H); 1.19 (d, J=7.2 Hz, 3H); $^{13}C$ NMR (62.5 MHz, $CDCl_3$) δ 175.2; 68.6; 59.9; 46.7; 19.8; 13.7; 12.8; MS (CI) m/z 147 $[M+H]^+$.

Ethyl (2S,3S)-anti-2-methyl-3-tetrahydropyranyloxy-butanoate (4)

Preparation with a Cation-Exchange Resin (H+ Form): Amberlyst® H15 (Marketed by Rohm and Haas)

Amberlyst® H15 (162 mg) was added to a stirred solution of ethyl (2S,3S)-2-methyl-3-hydroxybutanoate (3) (945 mg, 6.47 mmol) and dihydropyran (600 mg, 0.65 ml, 7.12 mmol) in heptane at 0° C. and the mixture was stirred at 0° C. for one hour and then at room temperature for 6 hours. The resin was removed by filtration and the solvent evaporated under vacuum. The residue was chromatographed on silica gel using, as eluent, heptane/EtOAc (20:1) to give ethyl (2S,3S)-anti-2-methyl-3-tetrahydropyranyloxybutanoate (4) (1.30 g, 87%).

Preparation with Pyridine Para-Toluenesulfonate (PPTS)

A solution of ethyl (2S,3S)-2-methyl-3-hydroxybutanoate (3) (5.245 g, 35.92 mmol) and of dihydropyran (3.929 g, 4.26 ml, 46.70 mmol) in dry dichloromethane containing PPTS (0.90 g, 3.59 mmol) was stirred for 24 hours at room temperature. The solvent was removed under vacuum and ether was added. The suspension was washed with half-saturated brine in order to remove the catalyst and then it was washed with saturated $NaHCO_3$ and brine, it was dried and evaporated. The residue was purified by means of chromatography on a silica gel column (heptane/EtOAc=20:1) in order to obtain ethyl (2S,3S)-anti-2-methyl-3-tetrahydropyranyloxybutanoate (4) (8.18 g, 99%).

Preparation of a Catalytic Quantity of Para-Toluene-Sulfonic Acid Monohydrate ($TsOH.H_2O$)

$TsOH.H_2O$ (3.2 mg, 0.017 mmol, 0.2%) was added at room temperature to a stirred solution of ethyl (2S,3S)-2-methyl-3-hydroxybutanoate (3) (1.22 g, 8.36 mmol) and dihydropyran (773 mg, 0.84 ml, 9.19 mmol) in toluene (17 ml). After stirring at the same temperature for 1 hour, the reaction was stopped by adding a saturated aqueous $NaHCO_3$ solution.

The mixture was extracted with toluene. The organic phase was washed with brine, dried over Na$_2$SO$_4$ and evaporated. Chromatography on a silica gel column (heptane/EtOAc=20:1) gave ethyl (2S,3S)-anti-2-methyl-3-tetrahydropyranyloxybutanoate (4) (1.91 g, 99%): IR (CHCl$_3$) 3009, 2982, 2945, 2872, 1727, 1455, 1381, 1324, 1262, 1235, 1190 cm$^{-1}$; $^1$H NMR (250 MHz, CDCl$_3$) δ 4.80 to 4.77 (m, 0.5H); 4.65 to 4.62 (m, 0.5H); 4.21 to 3.77 (m, 4H); 3.56 to 3.45 (m, 1H); 2.71 to 2.53 (m, 1H); 1.81 to 1.47 (m, 6H); 1.28 (t, J=7.2 Hz, 1.5H); 1.26 (t, J=7.1 Hz, 1.5H); 1.24 (d, J=6.2 Hz, 1.5H); 1.15 (d, J=7.1 Hz, 1.5H); 1.12 (d, J=6.2 Hz, 1.5H); 1.10 (d, J=7.1 Hz, 1.5H); $^{13}$C NMR (62.5 MHz, CDCl$_3$) δ 174.2; 99.4; 94.4; 75.8; 71.6; 62.1; 61.2; 59.6; 45.5; 30.7; 30.5; 25.1; 19.4; 18.7; 18.1; 14.9; 13.8; 12.0; 11.9; MS (CI) m/z 231 [M+H]$^+$. Analysis: Calculated for C$_{12}$H$_{22}$O$_4$: C, 62.58; H, 9.63; Found: C, 62.71; H, 9.67.

(2R,3S)-2-methyl-3-tetrahydropyranyloxybutanol (5)

A solution of ethyl (2S,3S)-2-methyl-3-tetrahydropyranyloxybutanoate (4) (8.18 g, 35.56 mmol) at 0° C. was added dropwise to a stirred suspension of LiAlH$_4$ (2.70 g, 71.12 mmol) in THF/toluene (2:1) (178 ml). The reaction mixture is stirred at 0° C. for 30 minutes, and then at room temperature for 30 minutes. The reaction is neutralized by means of the "Fieser treatment"; the reaction was treated by successively adding dropwise 2.7 ml of ice-cold water, 2.7 ml of a 15% aqueous NaOH solution, and 3×2.7 ml of ice-cold water. After having stirred for at least 30 minutes, the mixture is filtered on Celite. The precipitated aluminum salts were then washed with EtOAc. The solvent was evaporated, the residual oil was purified by means of flash chromatography on a silica gel column (heptane/EtOAc=5:1 and then 2:1) in order to obtain (2R,3S)-2-methyl-3-tetrahydropyranyloxybutanol (5) in the form of a colorless oil (6.59 g, 99%): $^1$H NMR (250 MHz, CDCl$_3$) δ 4.69 to 4.67 (m, 0.5H); 4.58 to 4.56 (m, 0.5H); 3.98 to 3.43 (m, 5H); 1.80 to 1.48 (m, 7H); 1.29 (d, J=6.3 Hz, 1.5H); 1.18 (d, J=6.1 Hz, 1.5H); 0.95 (d, J=7.0 Hz, 1.5H); 0.94 (d, J=7.0 Hz, 1.5H); $^{13}$C NMR (50 MHz, CDCl$_3$) δ 99.9; 97.4; 78.4; 74.9; 65.2; 64.2; 62.7; 41.2; 40.6; 31.3; 31.0; 25.3; 25.1; 20.7; 19.8; 18.9; 17.5; 14.0; 13.0; MS (CI) m/z 189 [M+H]$^+$. HRMS calculated for C$_{10}$H$_{21}$O$_3$ (M+H), 189.14906; found, 189.14755.

(2S,3S)-2-methyl-3-tetrahydropyranyloxybutyraldehyde (6)

Oxidation with TEMPO

An aqueous NaOCl solution (11 mmol, 5.3 ml of a 12.5% solution) and NaHCO$_3$ (2.43 g, 29 mmol) was added dropwise, over a period of 1 hour, to a cold (0° C.), rapidly stirred (>1000 rpm), biphasic mixture consisting of (2R,3S)-2-methyl-3-tetrahydropyranyloxybutanol (5) (1.88 g, 10 mmol), TEMPO with free radicals (31.25 mg, 2%), sodium bromide (1.029 g, 10 mmol), toluene (30 ml), EtOAc (30 ml) and H$_2$O (5 ml). The aqueous phase was separated and washed with Et$_2$O (50 ml). The combined organic phases were washed with a KI solution (80 mg) dissolved in aqueous 10% KHSO$_4$ (20 ml), and then with a 10% aqueous sodium thiosulfate solution (10 ml), brine (20 ml), and dried (MgSO$_4$). Filtration and concentration under vacuum gave the desired aldehyde 6 (1.72 g, 92%) which was used for the next reactions without further purification.

Oxidation with Py.SO$_3$/DMSO

The Py.SO$_3$ complex (7.06 g, 44.36 mmol) was added in portions at 0° C. to a solution of (2R,3S)-2-methyl-3-tetrahydropyranyloxybutanol (5) (1.39 g, 7.39 mmol) and anhydrous Et$_3$N (4.94 g, 6.78 ml, 48.77 mmol) in DMSO (25 ml). The reaction mixture was stirred at 0° C. for 3 hours, and then at room temperature for 1 hour, and then it was divided between water and ether. The aqueous layer was extracted with ether. The combined ether extracts were washed with 1M HCl, water, saturated NaHCO$_3$, brine, and they were dried over Na$_2$SO$_4$ and evaporated in order to obtain crude (2S,3S)-2-methyl-3-tetrahydropyranyloxybutyraldehyde (6) (1.39 g, 100%) which was used directly for the next reaction without purification: $^1$H NMR (250 MHz, CDCl$_3$) δ 9.78 (d, J=2.7 Hz, 0.5H); 9.74 (d, J=2.0 Hz, 0.5H); 4.76 to 4.62 (m, 1H); 4.15 to 3.73 (m, 2H); 3.53 to 3.43 (m, 1H); 2.62 to 2.46 (m, 1H); 1.82 to 1.51 (m, 6H); 1.29 (d, J=6.2 Hz, 1.5H); 1.18 (d, J=6.2 Hz, 1.5H); 1.11 (d, J=7.2 Hz, 1.5H); 1.07 (d, J=7.1 Hz, 1.5H); $^{13}$C NMR (62.5 MHz, CDCl$_3$) δ 203.5; 203.1; 99.0; 95.1; 74.4; 71.0; 62.0; 51.6; 51.1; 30.5; 25.0; 19.2; 19.1; 18.6; 16.0; 9.7; 9.1; MS (CI) m/z 187. [M+H]$^+$.

(S)-N-[(2R,3S)-2-methyl-3-tetrahydropyranyloxybutylidene]-p-toluenesulfinamide (7)

Ti(OEt)$_4$ (1.71 g, 1.57 ml, 7.5 mmol, 5 eq.) was added dropwise, at room temperature, to a mixture of (S)-(+)-p-toluenesulfinamide (233 mg, 1.50 mmol) and (2S,3S)-2-methyl-3-benzyloxybutyraldehyde (6) (280 mg, 1.50 mmol) in dichloromethane (25 ml). The solution was refluxed under argon for 5.5 hours. The reaction was neutralized at 0° C. adding water (25 ml). The cloudy solution was filtered on Celite and the filter cake was washed with dichloromethane (2×25 ml). The phases were separated, the aqueous phase was extracted with dichloromethane and the combined organic portions were dried over Na$_2$SO$_4$ and they were concentrated. Flash chromatography on a silica gel column (heptane/EtOAc=6:1) produced (S)-N-[(2R,3S)-2-methyl-3-tetrahydropyranyloxybutylidene]-p-toluenesulfinamide (7) (375 mg, 77%): IR (CHCl$_3$) 3010, 2976, 2946, 2878, 2854, 1620, 1598, 1494, 1455, 1443, 1380, 1354, 1214 cm$^{-1}$; $^1$H NMR (250 MHz, CDCl$_3$) δ 8.31 (d, J=5.8 Hz, 0.5H); 8.23 (d, J=5.3 Hz, 0.5H); 7.55 (m, 2H); 7.29 (m, 2H); 4.79 to 4.70 (m, 0.5H); 4.55 to 4.51 (m, 0.5H); 4.00 to 3.82 (m, 1.5H); 3.77 to 3.70 (m, 0.5H); 3.48 to 3.41 (m, 1H); 2.84 to 2.64 (m, 1H); 2.39 (s, 3H); 1.78 to 1.41 (m, 6H); 1.25 (d, J=6.4 Hz, 1.5H); 1.14 (d, J=5.7 Hz, 3H); 1.14 (d, J=7.1 Hz, 1.5H); 1.09 (d, J=7.0 Hz, 1.5H); $^{13}$C NMR (75 MHz, CDCl$_3$) δ 169.2; 168.6; 141.9; 141.8; 141.2; 129.4; 124.4; 124.2; 99.6; 94.6; 76.4; 72.2; 62.3; 61.8; 45.6; 45.2; 30.6; 30.5; 25.2; 25.2; 21.1; 19.4; 19.1; 18.9; 16.3; 13.0; 12.5; MS (CI) m/z 324 [M+H]$^+$. HRMS: calculated for C$_{17}$H$_{26}$NO$_3$S (M+H), 324.16333; found, 324.16141.

(S)-N-[(1S,2R,3S)-1-cyano-2-methyl-3-tetrahydropyranyloxybutyl]-p-toluenesulfinamide (8)

Et$_2$AlCN (1.0 M in toluene, 1.28 ml, 1.28 mmol, 1.5 eq.) was added to an isopropanol solution (56 mg, 72 ml, 0.94 mmol, 1.1 eq.) in THF, and this solution was stirred at room temperature for 15 minutes.

The Et(OiPr)AlCN prepared above in THF at −70° C. was added to a solution of (S)—N-[(2R,3S)-2-methyl-3-tetrahydropyranyloxybutylidene]-p-toluenesulfinamide (7) (275 mg, 0.85 mmol) in tetrahydrofuran (THF). After 15 minutes, the reaction mixture was brought to room temperature, it was stirred and the disappearance of the sulfinamide (22 hours) was monitored by TLC. The reaction mixture was cooled to −70° C. and it was neutralized by adding aqueous NaHCO$_3$. The suspension was diluted with EtOAc, it was filtered on Celite and diluted with water and the aqueous phase was extracted with EtOAc (2×). The combined organic phases were washed with brine, they were dried and evaporated. Flash chromatography on a column (SiO$_2$, heptane/EtOAc=5:1 then 3:1) produced (S)—N-[(1S,2R,3S)-1-cyano-2-methyl-3-tetrahydropyranyloxybutyl]-p-toluenesulfinamide (8) (283 mg, 95%): IR (CHCl$_3$) 3672, 3368, 3252, 3012, 2948, 2857, 2243, 1598, 1492, 1454, 1380, 1343, 1236, 1174 cm$^{-1}$; $^1$H NMR (250 MHz, CDCl$_3$) δ 7.65 to 7.59 (m, 2H); 7.36 to 7.27 (m, 2H); 6.16 (d, J=9.6 Hz, 0.5H); 5.11 (m, 0.5H); 4.60 to 4.49 (m, 1.5H); 4.16 (dd, J=9.6, 2.6 Hz, 5H); 3.94 to 3.85 (m, 0.5H); 3.75 to 3.61 (m, 1H); 3.57 to 3.34 (m, 1.5H); 2.42 (s, 3H); 2.14 to 1.96 (m, 1H); 1.89 to 1.37 (m, 6H); 1.33 (d, J=6.2 Hz, 1.5H); 1.18 (d, J=6.1 Hz, 3H); 1.07 (d, J=6.9 Hz, 1.5H); 1.06 (d, J=6.9 Hz, 1.5H); $^{13}$C NMR (62.5 MHz, CDCl$_3$) δ 141.7; 141.5; 139.8; 139.4; 129.6; 125.8; 118.5; 117.5; 100.5; 96.7; 77.6; 72.1; 64.0; 62.3; 45.5; 44.4; 43.9; 30.9; 30.6; 25.1; 24.9; 21.1; 20.4; 19.3; 19.3; 16.9; 13.3; 11.6; MS (CI) m/z 351 [M+H]$^+$. HRMS: calculated for C$_{18}$H$_{27}$N$_2$O$_3$S (M+H), 351.17423; found, 351.17621.

(3S,4R,5S)-3-amino-4-methyl-5-methyl-2-oxotetrahydrofuran (9)

A solution of (S)-N-[(1S,2R,3S)-1-cyano-2-methyl-3-tetrahydropyranyloxybutyl]-p-toluenesulfinamide (8) (200 mg, 0.57 mmol) in 6N HCl (14 ml) was refluxed for 6 hours. The reaction mixture was washed with dichloromethane, and it was evaporated in order to obtain (3S,4R,5S)-3-amino-4-methyl-5-methyl-2-oxotetrahydrofuran hydrochloride (9) (94 mg, 100%). [α]$_D$=–18° (c 1.4; MeOH); IR (nujol) 3526, 2924, 2854, 1771, 1581, 1504, 1462, 1385, 1355, 1315, 1260, 1209 cm$^{-1}$; $^1$H NMR (250 MHz, D$_2$O) δ 4.61 to 4.54 (m, 2H); 2.72 (broad quintuplet, J=7.5 Hz, 1H); 1.40 (d, J=6.6 Hz, 3H); 1.11 (d, J=7.3 Hz, 3H); $^{13}$C NMR (50 MHz, D$_2$O) δ 174.3; 85.2; 52.3; 38.1; 19.5; 13.0; MS (CI) m/z 130 [M+H]$^+$. HRMS: calculated for C$_6$H$_{12}$NO$_2$ (M+H), 130.08680; found, 130.08604.

(2S,3R,4S)-4-hydroxyisoleucine (1) from (3S)-16 or from (9)

First Method:

LiOH.H$_2$O (16 mg, 0.37 mmol) was added to a solution of (3S,4R,5S)-3-amino-4-methyl-5-methyl-2-oxotetrahydrofuran (9) (28 mg, 0.17 mmol) in a THF/H$_2$O/methanol (MeOH) (1:1:10, 3 ml) mixture. The solution was stirred at room temperature for 4 hours. The solvent was evaporated. The residue was dissolved in water, and then it was passed through a column of ion-exchange resin Dowex 50WX8 (H+ form). The column was meticulously washed with water and the amino acid was eluted with 2M NH$_4$OH in order to obtain (2S,3R,4S)-4-hydroxyisoleucine (1) (16 mg, 70%).

Second Method:

LiOH.H$_2$O (4.22 g, 100.6 mmol) was added to a solution of (3S,4R,5S)-3-amino-4-methyl-5-methyl-2-oxotetrahydrofuran hydrochloride (9) (8.30 g, 50.3 mmol) or (3S,4R,5S)-3-amino-4-methyl-5-methyl-2-oxotetrahydrofuran (3S)-(16) in H$_2$O (250 ml). The solution was stirred at room temperature for 18 hours. After addition of acetic acid (2.9 ml, 50.3 mmol), the solvent was evaporated to complete dryness at room temperature using a rotary evaporator. The residue was crystallized from 90% ethanol so as to obtain (2S,3R,4S)-4-hydroxyisoleucine (1) (6.65 g, 90%): $^1$H NMR (250 MHz, D$_2$O) δ 3.84 (d, J=4.4 Hz, 1H); 3.78 (m, 1H); 1.87 (m, 1H); 1.19 (d, J=6.4 Hz, 3H); 0.91 (d, J=7.0 Hz, 3H); $^{13}$C NMR (50 MHz, D$_2$O) δ 174.5; 70.6; 57.7; 42.0; 21.4; 12.8; MS (CI) m/z (HCl salt) 184 [M+H]$^+$. Microanalysis: calculated for C$_6$H$_{13}$NO$_3$: C, 48.97; H, 8.90; N, 9.52; found, C, 49.04; H, 8.83; N, 9.60.

(2R,3S)-1-cyano-2-methyl-3-tetrahydropyranyloxy-N-benzylbutylamine (10)

Method 1

Benzylamine (346 mg, 353 ml, 3.23 mmol) was added at room temperature to a solution of the aldehyde 6 prepared above (500 mg, 2.69 mmol) in dichloromethane (9 ml), and the stirring was continued at room temperature for 2 hours. The reaction mixture was cooled to 0° C., and methanol (3 ml) and TMSCN (400 mg, 538 ml, 4.03 mmol) were successively introduced. After stirring at 0° C. for 2 hours and then at room temperature for 22 hours, the reaction mixture was separated in saturated NaHCO$_3$ and ether. The aqueous phase was extracted with ether, the ether extracts were washed with brine, they were dried and filtered on a short disk of Celite, and Na$_2$SO$_4$, and then evaporated. Flash chromatography on a silica gel column with, as eluent, heptane/EtOAc=10:1, produced (1R,2R,3S)-1-cyano-2-methyl-3-tetrahydropyranyloxy-N-benzylbutylamine (1R)-(10) and (1S,2R,3S)-1-cyano-2-methyl-3-tetrahydropyranyloxy-N-benzylbutylamine (1S)-(10) (735 mg in total, 90%).

(1R,2R,4S)-1-cyano-2-methyl-3-tetrahydropyranyloxy-N-benzylbutylamine (1R)-(10)

IR (CHCl$_3$) 3510, 3338, 3013, 2946, 2854, 1605, 1496, 1455, 1386, 1355, 1276, 1232 cm$^{-1}$, $^1$H NMR (250 MHz, CDCl$_3$) δ 7.39 to 7.26 (m, 5H); 4.66 to 4.64 (m, 0.5H); 4.58 to 4.55 (m, 0.5H); 4.05 (d, J=12.5 Hz, 1H); 3.99 to 3.65 (m, 4H); 3.51 to 3.43 (m, 1H); 2.06 to 1.92 (m, 1H); 1.78 to 1.38 (m, 6H); 1.28 (d, J=6.2 Hz, 1.5H); 1.14 (d, J=6.2 Hz, 1.5H); 1.07 (d, J=7.1 Hz, 1.5H); 1.04 (d, J=6.8 Hz, 1.5H); $^{13}$C NMR (62.5 MHz, CDCl$_3$) δ 138.8; 138.3; 128.4; 128.3; 128.2; 127.2; 127.0; 119.8; 119.7; 100.8; 95.9; 77.6; 71.8; 63.4; 62.4; 52.4; 52.1; 51.7; 42.8; 42.2; 31.0; 30.7; 25.1; 20.2; 19.8; 19.6; 16.8; 12.8; 12.7; MS (CI) m/z 303 [M+H]$^+$. HRMS: calculated for C$_{18}$H$_{27}$N$_2$O$_2$ (M+H), 303.20724; found, 303.20621.

(1S,2R,3S)-1-cyano-2-methyl-3-tetrahydropyranyloxy-N-benzylbutylamine (1S)-(10)

IR (CHCl$_3$) 3504, 3340, 3013, 2947, 2854, 1605, 1497, 1455, 1384, 1354, 1262, 1231 cm$^{-1}$; $^1$H NMR (250 MHz, CDCl$_3$) δ 7.35 to 7.26 (m, 5H); 4.60 (m, 1H); 4.12 to 4.05 (m, 1H); 3.94 to 3.58 (m, 4H); 3.52 to 3.40 (m, 1H); 2.03 to 1.89 (m, 1H); 1.79 to 1.46 (m, 6H); 1.25 (d, J=6.2 Hz, 1.5H); 1.11 (d, J=6.2 Hz, 1.5H); 1.05 (d, J=6.7 Hz, 1.5H); 1.03 (d, J=6.8 Hz, 1.5H); $^{13}$C NMR (62.5 MHz, CDCl$_3$) δ 138.6; 138.2; 128.3; 127.4; 127.2; 119.6; 119.1; 100.4; 96.2; 76.6; 71.7; 63.4; 62.9; 51.8; 51.5; 42.5; 42.3; 31.0; 30.9; 25.2; 20.1; 19.8; 18.7; 16.3; 12.7; 11.6; MS (CI) m/z 303 [M+H]$^+$. HRMS: calculated for C$_{18}$H$_{27}$N$_2$O$_2$ (M+H), 303.20724; found, 303.20876.

(2R,3S)-1-cyano-2-methyl-3-tetrahydropyranyloxy-N-benzylbutylamine (10)

Method 2

KCN (553 mg, 8.49 mmol) was added at room temperature to a solution of the aldehyde 6 prepared above (1.58 g, 8.49 mmol) and benzylamine hydrochloride (1.21 g, 8.49 mmol) in methanol (20 ml) and water (20 ml). After stirring at room temperature for 24 hours, the reaction mixture was separated in saturated NaHCO$_3$ and ether. The aqueous phase was extracted with ether, the ether extracts were washed with brine, they were dried and filtered on a short disk of Celite, and Na$_2$SO$_4$, and then evaporated. Flash chromatography on a silica gel column with, as eluent, heptane/EtOAc=10:1, produced (1R,2R,3S)-1-cyano-2-methyl-3-tetrahydropyranyloxy-N-benzylbutylamine (1R)-(10) and (1S,2R,3S)-1-cyano-2-methyl-3-tetrahydropyranyloxy-N-benzylbutylamine (1S)-(10) (2.097 g in total, 82%).

(3R,4R,5S)-3-N-benzylamino-4-methyl-5-methyl-2-oxotetrahydrofuran (3R)-(11) and (3S,4R,5S)-3-N-benzylamino-4-methyl-5-methyl-2-oxotetrahydrofuran (3S)-(11) from (1R,2R,3S)-1-cyano-2-methyl-3-tetrahydropyranyloxy-N- benzylbutylamine (1R)-(10) and (1S,2R,3S)-1-cyano-2-methyl-3-tetrahydropyranyloxy-N-benzylbutylamine (1S)-(10)

A solution of (1R,2R,3S)-1-cyano-2-methyl-3-tetrahydropyranyloxy-N-benzylbutylamine (1R)-(10) and of (1S,2R,3S)-1-cyano-2-methyl-3-tetrahydropyranyloxy-N-benzylbutylamine (1S)-(10) (375 mg, 1.24 mmol) in 6N HCl (25 ml) was refluxed for 6 hours. The reaction mixture was washed with dichloromethane and it was evaporated in order to obtain (3R,4R,5S)-3-N-benzylamino-4-methyl-5-methyl-2-oxotetrahydrofuran hydrochloride (3R)-(11) and (3S, 4R, 5S)-3-N-benzylamino-4-methyl-5-methyl-2-oxotetrahydrofuran hydrochloride (3S)-(11) (316 mg, 100%) in a ratio of 45:55.

(3S,4R,5S)-3-N-benzylamino-4-methyl-5-methyl-2-oxotetrahydrofuran (3S)-(11) from (1S,2R,3S)-1-cyano-2-methyl-3-tetrahydropyranyloxy-N-benzylbutylamine (1S)-(10)

A solution of (1S,2R,3S)-1-cyano-2-methyl-3-tetrahydropyranyloxy-N-benzylbutylamine (1S)-10 (34 mg, 0.11 mmol) in 6N HCl (2 ml) was refluxed for 6 hours. The reaction mixture was washed with dichloromethane, it was basified with saturated aqueous $NaHCO_3$, and it was extracted with EtOAc. The EtOAc extracts were washed with brine, they were dried and evaporated in order to obtain (3S,4R,5S)-3-N-benzylamino-4-methyl-5-methyl-2-oxotetrahydrofuran (a γ-lactone) (3S)-(11) (24 mg, 100%): $[\alpha]_D=-14°$ (c 2.2, $CHCl_3$); IR($CHCl_3$) 3528, 3333, 3088, 3066, 3029, 2981, 2935, 2875, 2822, 1770, 1605, 1496, 1455, 1384, 1361, 1300, 1229, 1178 $cm^{-1}$; $^1H$ NMR (250 MHz, $CDCl_3$) δ 7.38 to 7.18 (m, 5H); 4.31 (qd, J=6.5, 3.5 Hz, 1H); 3.93 (d, J=13.2 Hz, 1H); 3.86 (d, J=13.2 Hz, 1H); 3.61 (d, J=7.3 Hz, 1H); 2.26 (quintuplet-d, J=7.1, 3.4 Hz, 1H); 1.75 (broad s, 1H, NH), 1.36 (d, J=6.5 Hz, 3H); 1.07 (d, J=7.1 Hz, 3H); $^{13}C$ NMR (62.5 MHz, $CDCl_3$) δ 176.5; 139.3; 128.4; 128.1; 127.2; 81.5; 58.1; 52.1; 40.1; 19.6; 12.6; MS (CI) m/z (HCl salt) 220 [M+H]$^+$. The HCl salt: $^1H$ NMR (250 MHz, $D_2O$) δ 7.52 (m, 5H); 4.70 (d, J=7.7 Hz, 1H); 4.64 (m, 1H); 4.60. (d, J=13.1 Hz, 1H); 4.42 (d, J=13.1 Hz, 1H); 2.84 (quintuplet, J=7.2, 1H); 1.42 (d, J=6.7 Hz, 3H), 1.18 (d, J=7.2 Hz, 3H); $^{13}C$ NMR (62.5 MHz, $D_2O+CD_3OD$) δ 173.1; 131.2; 131.0; 130.3; 84.9; 58.1; 52.0; 38.3; 19.5; 13.8; HRMS: calculated for $C_{13}H_{18}NO_2$ (M+H), 220.13374; found, 220.13562.

(3R,4R,5S)-3-N-benzylamino-4-methyl-5-methyl-2-oxotetrahydrofuran (3R)-(11) from (1R,2R,3S)-1-cyano-2-methyl-3-tetrahydropyranyloxy-N-benzylbutylamine (1R)-(10)

A solution of (1R,2R,3S)-1-cyano-2-methyl-3-tetrahydropyranyloxy-N-benzylbutylamine (1R)-10 (20 mg, 0.066 mmol) in 6N HCl (1.5 ml) was refluxed for 6 hours. The reaction mixture was washed with dichloromethane, it was basified with saturated aqueous $NaHCO_3$ and it was extracted with EtOAc. The EtOAc extracts were washed with brine and they were dried and evaporated in order to obtain (3R,4R,5S)-3-N-benzylamino-4-methyl-5-methyl-2-oxotetrahydrofuran (a γ-lactone) (3R)-(11) (13.5 mg, 93%): $[\alpha]_D=+48°$ C. (c 2.4, $CHCl_3$); IR ($CHCl_3$) 3528, 3327, 3030, 2980, 2934, 2913, 2877, 1770, 1604, 1455, 1389, 1328, 1231, 1224, 1211, 1187 $cm^{-1}$; $^1H$ NMR (250 MHz, $CDCl_3$) δ 7.39 to 7.23 (m, 5H); 4.06 to 3.94 (m, 3H); 3.18 (d, J=11.4 Hz, 1H); 2.01 to 1.85 (m, 2H); 1.39 (d, J=6.1 Hz, 3H); 1.14 (d, J=6.5 Hz, 3H); $^{13}C$ NMR (62.5 MHz, $CDCl_3$) δ 177.0; 139.6; 128.3; 128.0; 127.0; 79.5; 63.4; 51.3; 45.4; 18.4; 14.3; MS (CI) m/z (HCl salt) 220 [M+H]$^+$. HCl salt: $^1H$ NMR (250 MHz, $D_2O$) δ 7.50 (m, 5H); 4.56 (d, J=12.9 Hz, 1H); 4.45 to 4.34 (m, 1H); 4.39 (d, J=12.9 Hz, 1H); 4.26 (d, J=11.5 Hz, 1H); 2.58 to 2.41 (m, 1H); 1.46 (d, J=6.2 Hz, 3H); 1.25 (d, J=6.5 Hz, 3H); $^{13}C$ NMR (62.5 MHz, $D_2O$) δ 173.0; 130.6; 130.4; 129.9; 82.6; 67.0; 61.4; 50.3; 42.0; 17.9; 13.6; HRMS: calculated for $C_{13}H_{18}NO_2$ (M+H), 220.13374; found, 220.13195.

(2S,3R,4S)-N-benzyl-4-hydroxyisoleucine (2S)-N-Bn-1 by alkaline hydrolysis of (3S)-11

A solution of lactone (3S)-11 (55 mg, 0.25 mmol) in $H_2O$ (2 ml) containing $LiOH.H_2O$ (12 mg, 0.27 mmol) was stirred for 2 hours at room temperature. After addition of AcOH (16 μl, 0.27 mmol), the solution was extracted with EtOAc (3×5 ml), dried over $Na_2SO_4$ and the solvent was evaporated to give (2S,3R,4S)-N-Bn-4-hydroxyisoleucine (2S)-N-Bn-1 (55 mg, 93%): $[\alpha]_D=-5°$ (c 0.9, $H_2O$); $^1H$ NMR (250 MHz, $D_2O$) δ 7.31 (5H); 4.13 (d, J=13.0 Hz, 1H); 3.95 (d, J=13.0 Hz, 1H); 3.53 (m, 2H); 1.68 (m, 1H); 1.01 (d, J=6.3 Hz, 3H); 0.95 (d, J=7.0 Hz, 3H); $^{13}C$ NMR (50 MHz, $D_2O$) δ 174.2; 131.2; 130.6; 130.3; 129.9; 71.3; 65.0; 51.2; 41.6; 21.4; 12.7.

(2R,3R,4S)-N-benzyl-4-hydroxyisoleucine (2R)-N-Bn-1 by alkaline hydrolysis of (3R)-11

(3R)-11 (197 mg, 0.9 mmol) was hydrolyzed in the same manner as described above to give (2R,3R,4S)-N-benzyl-4-hydroxyisoleucine (2R)-N-Bn-1 (205 mg, 96%): melting point=193-194° C. (decomposition); $[\alpha]_D=+24°$ (c 1, $H_2O$); $^1H$ NMR (250 MHz, $D_2O$) δ 7.48 (5H); 4.35 (d, J=13.1 Hz, 1H); 4.07 (d, J=13.1 Hz, 1H); 3.82 (m, 2H); 2.02 (m, 1H); 1.00 (d, J=6.1 Hz, 3H); 0.99 (d, J=7.1 Hz, 3H); $^{13}C$ NMR (50 MHz, $D_2O$) δ 174.7; 131.7; 130.8; 130.3; 129.9; 70.9; 62.2; 51.4; 40.1; 20.8; 12.7.

Cyclization of (2R)-N-Bn-1 into the Lactone (3R)-11

Trifluoroacetic acid (200 μl) was added to a solution of (2R)-N-Bn-1 (40 mg) in $H_2O$ (10 ml) and the solution was heated at 45° C. for 5 minutes. The solvent was evaporated using a rotary evaporator at 45° C. The residue was dissolved in EtOAc (10 ml), washed with a saturated $NaHCO_3$ solution, brine and dried over $Na_2SO_4$ to give the lactone (3R)-11 (33 mg, 89%).

(2S,3R,4S)-4-hydroxyisoleucine (1) from (11)

A solution of 11 (500 mg, 2.28 mmol) in $H_2O$ (20 ml) containing $LiOH.H_2O$ (100 mg) was stirred for 2 hours at room temperature. The end of the hydrolysis was confirmed by TLC (EtOAc/heptane=1:3). TFA (0.4 ml) was added to this solution and the solvent was evaporated using a rotary evaporator at 50° C. The residue was dissolved in $H_2O$. HPLC analysis demonstrated the complete disappearance of the peak corresponding to (2R)-N-Bn-1 and the reappearance of (3R)-11. The above solution was treated with EtOAc in order to remove the lactone (3R)-11 (63 mg, 38%) and the aqueous phase was treated with $H_2$ in the presence of 10% palladium on carbon (10 mg) for 6 hours at room temperature. After filtration of the catalyst, the solvent was condensed and passed through an ion-exchange resin Dowex 50WX8 (H+ form) with a 2M aqueous ammonia solution. The ninhydrin-positive fractions were collected and the solvent removed. The residue was recrystallized from $H_2O$/ethanol to give (2S, 3R,4S)-4-hydroxyleucine (1) (142 mg, 42%).

Catalytic Hydrogenolysis of (2S)-N-Bn-1

A solution of (2S)-N-Bn-1 (85 mg, 0.36 mmol) in $H_2O$ (10 ml) was treated with $H_2$ in the presence of 10% palladium on carbon (5 mg) for 6 h at room temperature. The catalyst was removed by filtration and the solvent evaporated. The residue was recrystallized from $H_2O$/MeOH to give (1) (50 mg, 93%): melting point=224° C.; $[\alpha]_D=+31.5°$ (c 1, $H_2O$); $^1H$ NMR (250 MHz, $D_2O$) δ 3.88 (d, J=4.4 Hz, 1H); 3.78 (m, 1H); 1.91 (m, 1H); 1.23 (d, J=6.4 Hz, 3H); 0.95 (d, J=7.0 Hz, 3H); $^{13}C$ NMR (50 MHz, $D_2O$) δ 174.2; 70.4; 57.5; 41.9; 21.3; 12.7; MS (ES) m/z 148 [M+H]$^+$.

Ethyl (2S,3S)-anti-2-methyl-3-benzyloxybutanoate (12)

Trifluoromethanesulfonic acid (0.09 ml) was added dropwise to a solution of ethyl (2S,3S)-anti-2-methyl-3-hydroxybutanoate (3) (1.0 g, 6.85 mmol) and benzyl 2,2,2-trichloroacetimidate (4.32 g, 17.12 mmol) in cyclohexane (20 ml) and dichloromethane (10 ml). The reaction mixture was stirred at room temperature for 24 hours. Saturated NaHCO$_3$ was added. The organic layer was extracted with dichloromethane. The organic extracts were combined, they were dried and concentrated. The resulting solid was filtered and it was washed with heptane. The filtrate was concentrated under vacuum and the resulting oil was chromatographed on a silica gel column eluting with heptane/ether=50:1 and then with heptane/EtOAc=20:1 in order to obtain (2S,3S)-anti-2-methyl-3-benzyloxybutanoate (12) (1.305 g, 81%).

(2R,3S)-2-methyl-benzyloxybutanol (13)

A solution of ethyl (2S,3S)-anti-2-methyl-3-benzyloxybutanoate (1.12 g, 4.75 mmol) at 0° C. was added dropwise to a stirred suspension of LiAlH$_4$ (360 mg, 9.50 mmol) in ether (48 ml). The reaction mixture was stirred at 0° C. for 30 min, and then at room temperature for 4 hours. The reaction was neutralized by means of the "Fieser treatment": the reaction was treated by successively adding dropwise 0.36 ml of ice-cold water, 0.36 ml of a 15% aqueous NaOH solution, and 3×0.36 ml of ice-cold water. After having stirred for at least 30 minutes, the mixture was filtered on Celite. The precipitated aluminum salts were then washed with EtOAc. The solvent was evaporated, the residual oil was purified by means of silica gel (heptane/EtOAc=5:1 and then 2:1) in order to obtain (2R,3S)-2-methyl-3-benzyloxybutanol (13) in the form of a colorless oil (673 mg, 73%): $[\alpha]_D$=+65° (c 3.0; CHCl$_3$); IR (CHCl$_3$) 3501, 3011, 2978, 2934, 2880, 1497, 1455, 1423, 1376, 1350, 1236 cm$^{-1}$; $^1$H NMR (250 MHz, CDCl$_3$) δ 7.39 to 7.25 (m, 5H); 4.66 (d, J=11.5 Hz, 1H); 4.46 (d, J=11.5 Hz, 1H); 3.65 (dd, J=10.9, 3.9 Hz, 1H); 3.57 (dd, J=10.9, 6.7 Hz, 1H); 3.49 (dq, J=6.8, 6.2 Hz, 1H); 2.85 (broad s, 1H, OH); 1.79 (sextuplet-d, J=7.0, 3.9 Hz, 1H); 1.25 (d, J=6.2 Hz, 3H); 0.90 (d, J=7.0 Hz, 3H); $^{13}$C NMR (62.5 MHz, CDCl$_3$) δ 138.3; 128.2; 127.5; 127.4; 79.0; 70.5; 66.0; 40.7; 16.7; 13.3; MS (CI) m/z 195 [M+H]$^+$. HRMS: calculated for C$_{12}$H$_{19}$O$_2$ (M+H), 195.13849; found, 195.13830.

(2S,3S)-2-methyl-3-benzyloxybutyraldehyde (14)

The Py.SO$_3$ complex (4.09 g, 25.67 mmol, 6.0 eq.) was added in portions at 0° C. to a solution of (2R,3S)-2-methyl-3-benzyloxybutanol (13) (830 mg, 4.28 mmol) and Et$_3$N (2.86 g, 3.93 ml, 28.25 mmol, 6.6 eq.) in DMSO (14 ml). The reaction mixture is stirred at 0° C. for 3.5 hours, and then at room temperature for 2 hours, and then it was divided between water and ether. The aqueous layer was extracted with ether. The combined ether extracts were washed with 1M HCl, waters saturated NaHCO$_3$, brine, and they were dried over Na$_2$SO$_4$ and evaporated in order to obtain crude (2S,3S)-2-methyl-3-benzyloxybutyraldehyde which was used directly for the next reaction without purification. $^1$H NMR (250 MHz, CDCl$_3$) δ 9.73 (d, J=2.4 Hz, 1H); 4.63 (d, J=11.7 Hz, 1H); 4.44 (d, J=11.7 Hz, 1H); 3.81 (quintuplet, J=6.4 Hz, 1H); 2.57 (quintuplet-d, J=7.0; 2.4 Hz, 1H); 1.25 (d, J=6.2 Hz, 3H); 1.09 (d, J=7.1 Hz, 3H).

(2R,3S)-1-cyano-2-methyl-3-benzyloxy-N-benzylbutylamine (15)

Benzylamine (550 mg, 561 μl, 5.14 mmol) was added at room temperature to a solution of the aldehyde prepared above in dichloromethane (21 ml) in the presence of MgSO$_4$, and the stirring was continued overnight at room temperature. The reaction mixture was filtered on Celite and the filtrate was evaporated in order to obtain the crude imine. TMSCN (637 mg, 856 μl, 6.42 mmol) was added to a solution of the imine in dichloromethane (15 ml) and methanol (5 ml) at 0° C. After stirring at 0° C. for 1 hour and then at room temperature overnight, the reaction mixture was separated in saturated NaHCO$_3$ and ether. The aqueous phase was extracted with ether, the ether extracts were washed with brine, they were dried and filtered on a short disk of Celite and Na$_2$SO$_4$ and they were evaporated. Flash chromatography on a silica gel column with, as eluent, heptane/EtOAc=10:1 produced (1R,2R,3S)-1-cyano-2-methyl-3-benzyloxy-N-benzylbutylamine (1R)-15 (705 mg, 53%) and (1S,2R,3S)-1-cyano-2-methyl-3-benzyloxy-N-benzylbutylamine (1S)-(15) (400 mg, 30%) [(IR)/(IS)=1.76:1].

(1R,2R,3S)-1-cyano-2-methyl-3-benzyloxy-N-benzylbutylamine (1R)-(15) $[\alpha]_D$=+114° (c 4.4; CHCl$_3$); IR (CHCl$_3$) 3338, 3089, 3067, 3030, 3013, 2979, 2936, 2905, 2882, 2226, 1605, 1587, 1497, 1455, 1386, 1377, 1363, 1340, 1231, 1222, 1216 cm$^{-1}$; $^1$H NMR (250 MHz, CDCl$_3$) δ 7.32 to 7.18 (m, 10H); 4.58 (d, J=10.6 Hz, 1H); 4.34 (d, J=10.6 Hz, 1H); 3.95 (d, J=12.7 Hz, 1H); 3.63 (d, J=12.7 Hz, 1H); 3.74 to 3.62 (m, 2H); 2.22 (broad s, 1H, NH); 2.07 to 1.94 (m, 1H); 1.24 (d, J=6.1 Hz, 3H); 1.05 (d, J=7.1 Hz, 3H); $^{13}$C NMR (62.5 MHz, CDCl$_3$) δ 138.4; 137.9; 128.2; 127.9; 127.5; 127.1; 119.6; 77.1; 71.0; 53.4; 51.7; 42.7; 17.0; 13.7; MS (CI) m/z 309 [M+H]$^+$. HRMS: calculated for C$_{20}$H$_{25}$N$_2$O (M+H), 309.19668; found, 309.19396.

(1S,2R,3S)-1-cyano-2-methyl-3-benzyloxy-N-benzylbutylamine (1S)-(15) $[\alpha]_D$=−12° (c 3.6; CHCl$_3$); IR (CHCl$_3$) 3343, 3090, 3068, 3031, 3013, 2979, 2935, 2880, 2226, 1605, 1587, 1497, 1455, 1386, 1378, 1359, 1333, 1232 cm$^{-1}$; $^1$H NMR (250 MHz, CDCl$_3$) δ 7.34 to 7.22 (m, 10H); 4.59 (d, J=11.2 Hz, 1H); 4.37 (d, J=11.2 Hz, 1H); 4.04 (d, J=12.8 Hz, 1H); 3.97 (d, J=4.7 Hz, 1H); 3.79 (d, J=12.8 Hz, 1H); 3.50 (dq, J=8.8; 6.1 Hz, 1H); 2.07 to 1.93 (m, 1H); 1.62 (broad s, 1H, NH); 1.22 (d, J=6.0 Hz, 3H); 1.04 (d, J=6.9 Hz, 3H); $^{13}$C NMR (62.5 MHz, CDCl$_3$) δ 138.3; 138.0; 128.4; 128.3; 127.6; 127.5; 127.4; 119.1; 76.0; 70.8; 51.9; 51.5; 42.4; 16.4; 11.7; MS (CI) m/z 309 [M+H]$^+$. HRMS: calculated for C$_{20}$H$_{25}$N$_2$O (M+H), 309.19668; found, 309.19321.

(3R,4R,5S)-3-N-benzylamino-4-methyl-5-methyl-2-oxo-tetrahydrofuran (3R)-(11)

A solution of (1R,2R,3S)-1-cyano-2-methyl-3-benzyloxy-N-benzylbutylamine (1R)-(15) (220 mg, 0.71 mmol) was refluxed in 6N HCl (7 ml) for 6 hours. The reaction mixture was washed with dichloromethane, it was basified with saturated aqueous NaHCO$_3$, and it was extracted with EtOAc. The EtOAc extracts were washed with brine, they were dried and evaporated. Preparative TLC on silica gel (heptane/Et$_2$O=1:1) produced (3R,4R,5S)-3-N-benzylamino-4-methyl-5-methyl-2-oxo-tetrahydrofuran in the form of a colorless oil (124 mg, 80%): $[\alpha]_D$=+48° (c 2.4; CHCl$_3$); IR (CHCl$_3$) 3528, 3327, 3030, 2980, 2934, 2913, 2877, 1770, 1604, 1455, 1389, 1328, 1231, 1224, 1211, 1187 cm$^{-1}$; $^1$H NMR (250 MHz, CDCl$_3$) δ 7.39 to 7.23 (m, 5H); 4.06 to 3.94 (m, 3H); 3.18 (d, J=11.4 Hz, 1H); 2.01 to 1.85 (m, 2H); 1.39 (d, J=6.1 Hz, 3H); 1.14 (d, J=6.5 Hz, 3H); $^{13}$C NMR (62.5 MHz, CDCl$_3$) δ 177.0; 139.6; 128.3; 128.0; 127.0; 79.5; 63.4; 51.3; 45.4; 18.4; 14.3; MS (CI) m/z (HCl salt) 220 [M+H]$^+$. The HCl salt: $^1$H NMR (250 MHz, D$_2$O) δ 7.50 (m, 5H); 4.56 (d, J=12.9 Hz, 1H); 4.45 to 4.34 (m, 1H); 4.39 (d, J=12.9 Hz, 1H); 4.26 (d, J=11.5 Hz, 1H); 2.58 to 2.41 (m, 1H); 1.46 (d, J=6.2 Hz, 3H); 1.25 (d, J=6.5 Hz, 3H); $^{13}$C NMR (62.5 MHz, D$_2$O) δ 173.0; 130.6; 130.4; 129.9; 82.6; 67.0; 61.4; 50.3;

42.0; 17.9; 13.6. HRMS: calculated for $C_{13}H_{18}NO_2$ (M+H), 220.13374; found, 220.13195.

(3S,4R,5S)-3-N-benzylamino-4-methyl-5-methyl-2-oxo-tetrahydrofuran (3S)-(11)

A solution of (1S,2R,3S)-1-cyano-2-methyl-3-benzyloxy-N-benzylbutylamine (1S)-(15) (300 mg, 0.97 mmol) in 6N HCl (10 ml) was refluxed for 6 hours. The reaction mixture was washed with dichloromethane, it was basified with saturated aqueous $NaHCO_3$, and it was extracted with EtOAc. The EtOAc extracts were washed with brine, they were dried and evaporated. Preparative TLC on silica gel (dichloromethane/acetone=25:1) produced (3S,4R,5S)-3-N-benzylamino-4-methyl-5-methyl-2-oxotetrahydrofuran in the form of a colorless oil (117 mg, 55%): $[\alpha]_D=-14°$ (c 2.2; $CHCl_3$); IR ($CHCl_3$) 3528, 3333, 3088, 3066, 3029, 2981, 2935, 2875, 2822, 1770, 1605, 1496, 1455, 1384, 1361, 1300, 1229, 1178 $cm^{-1}$; $^1H$ NMR (250 MHz, $CDCl_3$) δ 7.38 to 7.18 (m, 5H); 4.31 (qd, J=6.5, 3.5 Hz, 1H); 3.93 (d, J=13.2 Hz, 1H); 3.86 (d, J=13.2 Hz, 1H); 3.61 (d, J=7.3 Hz, 1H); 2.26 (quintuplet-d, J=7.1, 3.4 Hz, H); 1.75 (broad s, 1H, NH); 1.36 (d, J=6.5 Hz, 3H); 1.07 (d, J=7.1 Hz, 3H); $^{13}C$ NMR (62.5 MHz, $CDCl_3$) δ 176.5; 139.3; 128.4; 128.1; 127.2; 81.5; 58.1; 52.1; 40.1; 19.6; 12.6; MS (CI) m/z (HCl salt) 220 [M+H]$^+$. The HCl salt: $^1H$ NMR (250 MHz, $D_2O$) δ 7.52 (m, 5H); 4.70 (d, J=7.7 Hz, 1H); 4.64 (m, 1H); 4.60 (d, J=13.1 Hz, 1H); 4.42 (d, J=13.1 Hz); 2.84 (quintuplet, J=7.2 Hz, 1H); 1.42 (d, J=6.7 Hz, 3H); 1.18 (d, J=7.2 Hz, 3H); $^{13}C$ NMR (62.5 MHz, $D_2O$+$CD_3OD$) δ 173.1; 131.2; 131.0; 130.3; 84.9; 58.1; 52.0; 38.3; 19.5; 13.8. HRMS: calculated for $C_{13}H_{18}NO_2$ (M+H), 220.13374; found, 220.13562.

(3R,4R,5S)-3-amino-4-methyl-5-methyl-2-oxotetrahydrofuran (3R)-(16)

A suspension of (3R,4R,5S)-3-N-benzylamino-4-methyl-5-methyl-2-oxotetrahydrofuran hydrochloride (120 mg, 0.47 mmol) and 10% Pd—C (24 mg) in methanol (10 ml) was hydrogenated at room temperature at atmospheric pressure overnight. The catalyst was removed by filtration and the solvent was evaporated in order to obtain (3R,4R,5S)-3-amino-4-methyl-5-methyl-2-oxotetrahydrofuran (78 mg, 100%): $[\alpha]_D=-3.4°$ (c 1.6, MeOH); IR (nujol) 3411, 2923, 2853, 1783, 1762, 1588, 1557, 1491, 1457, 1390, 1340, 1300, 1207 $cm^{-1}$; $^1H$ NMR (300 MHz, $D_2O$) δ4.47 (dq, J=9.7; 6.2 Hz, 1H); 4.19 (d, J=11.7 Hz, 1H); 2.46 to 2.32 (m, 1H); 1.49 (d, J=6.2 Hz, 3H); 1.29 (d, J=6.6 Hz, 3H); $^{13}C$ NMR (62.5 MHz, $D_2O$) δ 174.1; 83.1; 56.5; 43.5; 18.1; 13.2; MS (CI) m/z 130 [M+H]$^+$. HRMS: calculated for $C_6H_{12}NO_2$ (M+H), 130.08680; found, 130.08625.

(3S,4R,5S)-3-amino-4-methyl-5-methyl-2-oxotetrahydrofuran (3S)-(16)

A suspension of (3S,4R,5S)-3-N-benzylamino-4-methyl-5-methyl-2-oxotetrahydrofuran hydrochloride (110 mg, 0.43 mmol) and 10% Pd—C (22 mg) in methanol (9 ml) was hydrogenated at room temperature, at atmospheric pressure, overnight. The catalyst was removed by filtration. The solvent was evaporated in order to obtain (3S,4R,5S)-3-amino-4-methyl-5-methyl-2-oxotetrahydrofuran (71 mg, 100%): $[\alpha]_D=-18°$ (c 1.4, MeOH); IR (nujol) 3526, 2924, 2854, 1771, 1581, 1504, 1462, 1385, 1355, 1315, 1265, 1209 $cm^{-1}$; $^1H$ NMR (250 MHz, $D_2O$) δ 4.61 to 4.54 (m, 2H); 2.72 (broad quintuplet, J=7.5 Hz, 1H); 1.40 (d, J=6.6 Hz, 3H); 1.11 (d, J=7.3 Hz, 3H); $^{13}C$ NMR (50 MHz, $D_2O$) δ 174.3; 85.2; 52.3; 38.1; 19.5; 13.0; MS (CI) m/z 130 [M+H]$^+$. HRMS: calculated for $C_6H_{12}NO_2$ (M+H), 130.08680; found, 130.08604.

(3R,4R,5S)-3-N-benzylamino-4-methyl-5-methyl-2-oxotetrahydrofuran (3R)-(11) from (1R,2R,3S)-1-cyano-2-methyl-3-tetrahydropyranyloxy-N-benzylbutylamine (1R)-(10)

A solution of (1R,2R,3S)-1-cyano-2-methyl-3-tetrahydropyranyloxy-N-benzylbutylamine (1R)-(10) (25 mg, 0.083 mmol) in 6N HCl (2 ml) was refluxed for 6 hours. The reaction mixture was washed with dichloromethane and it was evaporated in order to obtain (3R,4R,5S)-3-benzylamino-4-methyl-5-methyl-2-oxotetrahydrofuran hydrochloride (3R)-(11) (21 mg, 100%).

(3S,4R,5S)-3-N-benzylamino-4-methyl-5-methyl-2-oxotetrahydrofuran (3S)-(11) from (1S,2R,3S)-1-cyano-2-methyl-3-tetrahydropyranyloxy-N-benzylbutylamine (1s)-(10)

A solution of (1S,2R,3S)-1-cyano-2-methyl-3-tetrahydropyranyloxy-N-benzylbutylamine (34 mg, 0.11 mmol) in 6N HCl (2 ml) was refluxed for 6 hours. The reaction mixture was washed with dichloromethane, it was basified with saturated aqueous $NaHCO_3$, and it was extracted with EtOAc. The EtOAc extracts were washed with brine, they were dried and evaporated in order to obtain (3S,4R,5S)-3-N-benzylamino-4-methyl-5-methyl-2-oxotetrahydrofuran (a γ-lactone) (24 mg, 100%).

(2R,3S)-1-cyano-2-methyl-3-tetrahydropyranyloxy-N-[(S)-1'-phenylethyl]butylamine (17)

(S)-(−)-1-phenylethylamine (211 mg, 225 μl, 1.74 mmol) was added at room temperature to a solution of (2S,3S)-2-methyl-3-tetrahydropyranyloxybutyraldehyde (6) (270 mg, 1.45 mmol) in dichloromethane (6 ml), and the stirring was continued at room temperature for 2 hours. The reaction mixture was cooled to 0° C., and methanol (2 ml) and TMSCN (216 mg, 290 μl, 2.18 mmol) were successively introduced. After stirring at 0° C. for 2 hours and then at room temperature for 22 hours, the reaction mixture was separated in saturated $NaHCO_3$ and ether. The aqueous phase was extracted with ether, the ether extracts were washed with brine, they were dried and filtered on a short disk of Celite and $Na_2SO_4$ and then evaported. Flash chromatography on a silica gel column with, as eluent, a heptane/EtOAc=10:1 then 8:1 mixture produced (1R,2R,3S)-1-cyano-2-methyl-3-tetrahydropyranyloxy-N-[(S)-1'-phenylethyl]butylamine (1R)-(17) and (1S,2R,3S)-1-cyano-2-methyl-3-tetrahydropyranyloxy-N-[(S)-1'-phenylethyl]butylamine (1S)-(17) (414 mg in total, 90%) in the ratio of about 1:3.

(1R,2R,3S)-1-cyano-2-methyl-3-tetrahydropyranyloxy-N-[(S)-1'-phenylethyl]butylamine (1R)-17 and (1S,2R,3S)-1-cyano-2-methyl-3-tetrahydropyranyloxy-N-[(S)-1'-phenylethyl]butylamine (1S)-17

First Method:

(S)-(−)-phenylethylamine hydrochloride (1.038 g, 6.61 mmol) and KCN (432 mg, 6.61 mmol) were added at room temperature to a suspension of (2S,3S)-2-methyl-3-tetrahydropyranyloxybutyraldehyde (6) (1.23 g, 6.61 mmol) in methanol (33 ml) and water (33 ml). After continuing the stirring at room temperature for 24 hours, the reaction mixture was separated in saturated $NaHCO_3$ and ethyl acetate. The aqueous phase was extracted with ethyl acetate, and the organic extracts were washed with brine, they were dried and filtered on a short disk of Celite and $Na_2SO_4$ and then evaporated. Flash chromatography on a silica gel column with, as eluent, a heptane/EtOAc=10:1 then 8:1 mixture produced the mixture of (1R,2R,3S)-1-cyano-2-methyl-3-tetrahydropyranyloxy-N-[(S)-1'-phenylethyl]butylamine (1R)-(17) and (1S, 2R,3S)-1-cyano-2-methyl-3-tetrahydropyranyloxy-N-[(S)-1'-phenylethyl]butylamine (1S)-(17) (1.73 g, 83%).

Second Method: c(S)-(−)-phenylethylamine hydrochloride (1.038 g, 6.61 mmol) and KCN (432 mg, 6.61 mmol) were added at 0° C. to a suspension of (2S,3S)-2-methyl-3-tetrahydropyranyloxybutyraldehyde (6) (1.23 g, 6.61 mmol) in methanol (33 ml) and water (33 ml). After continuing the stirring at 0° C. for 30 minutes and then at room temperature for 48 hours, the reaction mixture was separated in water and ethyl acetate. The aqueous phase was extracted with ethyl acetate, the organic extracts were washed with brine, they were dried and filtered on a short disk of Celite and $Na_2SO_4$ and then evaporated. Flash chromatography on a silica gel column with, as eluent, a heptane/EtOAc=10:1 then 8:1 mixture produced the mixture of (1R,2R,3S)-1-cyano-2-methyl-3-tetrahydropyranyloxy-N-[(S)-1'-phenylethyl]butylamine (1R)-(17) and (1S,2R,3S)-1-cyano-2-methyl-3-tetrahydropyranyloxy-N-[(S)-1'-phenylethyl]butylamine (1S)-(17) (1.73 g, 83%).

(1S,2R,3S)-1-cyano-2-methyl-3-tetrahydropyranyloxy-N-[(S)-1'-phenylethyl]butylamine (1S)-(17)

IR ($CHCl_3$) 3500, 3316, 3028, 3012, 2968, 2947, 2854, 2226, 1494, 1453, 1376, 1356, 1275, 1260, 1234, 1186, 1132 $cm^{-1}$; $^1H$ NMR (250 MHz, $CDCl_3$) δ 7.39 to 7.23 (m, 5H); 4.59 (m, 0.5H); 4.50 to 4.47 (m, 0.5H); 4.11 to 4.03 (m, 1H); 3.88 to 3.74 (m, 1H); 3.68 to 3.55. (m, 1H); 3.46 to 3.40 (m, 2H); 1.92 to 1.34 (m, 7H); 1.40 (d, J=6.5 Hz, 1.5H); 1.38 (d, J=6.4 Hz, 1.5H); 1.15 (d, J=6.2 Hz, 1.5H); 1.06 (d, J=6.1 Hz, 1.5H); 1.02 (d, J=6.9 Hz, 1.5H); 1.00 (d, J=6.9 Hz, 1.5H); $^{13}C$ NMR (62.5 MHz, $CDCl_3$) δ 143.6; 143.1; 128.6; 128.5; 127.5; 127.4; 127.0; 126.9; 120.1; 119.5; 100.2; 96.0; 76.4; 71.4; 63.2; 62.7; 56.6; 56.4; 50.5; 50.4; 42.7; 31.0; 30.7; 25.3; 24.7; 24.6; 19.9; 19.7; 18.5; 16.4; 13.1; 11.7; MS (CI) m/z 317 $[M+H]^+$. HRMS: calculated for $C_{19}H_{29}N_2O_2$ (M+H), 317.22289; found, 317.22647.

(3S,4R,5S)-3-N-[(S)-1'-phenylethylamino]-4-methyl-5-methyl-2-oxotetrahydrofuran (3S)-(18) and (3R,4R,5S)-3-N-[(S)-1'-phenylethylamino]-4-methyl-5-methyl-2-oxo-tetrahydrofuran (3R)-(18)

A solution of (2R, 3S)-1-cyano-2-methyl-3-pyranyloxy-N-[(S)-1'-phenylethyl]butylamine (17) (180 mg, 0.57 mmol) in 6N HCl (11 ml) was refluxed for 6 hours. The reaction mixture was washed with EtOAc/heptane. From there, two methods made it possible to obtain either a mixture of compounds (3S)-18 and (3R)-18, or compound (3S)-18 alone.

The first method is the following: the washed reaction mixture was basified with saturated aqueous $NaHCO_3$ and it was extracted with EtOAc. The EtOAc extracts were washed with brine, they were dried and evaporated. Flash chromatography on a silica gel column (heptane/EtOAc=6:1) produced (3S,4R,5S)-3-N-[(S)-1'-phenylethylamino]-4-methyl-5-methyl-2-oxo-tetrahydrofuran (3S)-(18) (57 mg, 43%) and (3R,4R,5S)-3-N-[(S)-1'-phenylethylamino]-4-methyl-5-methyl-2-oxotetrahydrofuran (3R)-(18) (16 mg, 12%) [(3S)/(3R)=3.5:1].

The second method is the following:

The water contained in the washed reaction mixture was removed by total evaporation. Crystallization is then carried out with isopropanol in order to obtain (3S,4R,5S)-3-N-[(S)-1'-phenylethylamino]-4-methyl-5-methyl-2-oxotetrahydrofuran (3S)-(18) with a yield, from compound (6), of 53%.

(3R,4R,5S)-3-N-[(S)-1'-phenylethylamino]-4-methyl-5-methyl-2-oxotetrahydrofuran (3R)-(18) $[α]_D$=−39° (c 0.7, $CHCl_3$); IR ($CHCl_3$) 3693, 3329, 3030, 2967, 2933, 2877, 1765, 1603, 1494, 1453, 1388, 1329, 1247, 1175 $cm^{-1}$; $^1H$ NMR (250 MHz, $CDCl_3$) δ 7.38 to 7.24 (m, 5H); 4.01 (q, J=6.6 Hz, 1H); 3.89 (qd, J=6.1, 9.7 Hz, 1H); 3.08 (d, J=11.1 Hz, 1H); 2.05 (broad s, 1H, NH); 1.91 (m, 1H); 1.38 (d, J=6.6 Hz, 3H); 1.35 (d, J=6.1 Hz, 3H); 1.12 (d, J=6.5 Hz, 3H); $^{13}C$ NMR (62.5 MHz, $CDCl_3$) δ 177.2; 144.7; 128.7; 127.2; 126.4; 79.5; 61.9; 56.5; 46.9; 24.7; 18.4; 14.8; MS (CI) m/z 234 $[M+H]^+$. HRMS: calculated for $C_{14}H_{20}NO_2$ (M+H), 234.14939; found, 234.15006.

(3S,4R,5S)-3-N-[(S)-1'-phenylethylamino]-4-methyl-5-methyl-2-oxotetrahydrofuran (3S)-(18) $[α]_D$=−94° (c 1.7, $CHCl_3$); IR ($CHCl_3$) 3568, 3330, 3028, 2980, 2933, 2875, 1769, 1494, 1453, 1383, 1354, 1301, 1224, 1220, 1172, 1146 $cm^{-1}$; $^1H$ NMR (250 MHz, $CDCl_3$) δ 7.39 to 7.22 (m, 5H); 4.23 (qd, J=6.5, 3.7 Hz, 1H); 4.17 (q, J=6.6 Hz, 1H); 3.38 (d, J=7.4 Hz, 1H); 1.89 (quintuplet-d, J=7.2, 3.7 Hz, 1H); 1.61 (broad s, 1H, NH); 1.38 (d, J=6.6 Hz, 3H); 1.27 (d, J=6.5 Hz, 3H); 0.99 (d, J=7.1 Hz, 3H); $^{13}C$ NMR (62.5 MHz, $CDCl_3$) δ 117.5; 144.8; 128.5; 127.3; 127.1; 81.3; 57.4; 57.0; 40.6; 24.6; 19.6; 12.7; MS (CI) m/z 234 $[M+H]^+$. The HCl salt: $^1H$ NMR (250 MHz, $D_2O$) δ 7.54 (s, 5H); 4.88 (q, J=6.9 Hz, 1H); 4.53 (q, J=6.6 Hz, 1H); 4.27 (d, J=7.7 Hz, 1H); 2.60 (quintuplet, J=7.3 Hz, 1H); 1.72 (d, J=6.9 Hz, 3H); 1.26 (d, J=6.7 Hz, 3H); 1.12 (d, J=7.2 Hz, 3H); $^{13}C$ NMR (62.5 MHz, $CD_3OD$) δ 171.6; 136.6; 130.9; 130.5; 129.3; 83.9; 59.3; 56.2; 39.0; 20.0; 19.8; 14.5. HRMS: calculated for $C_{14}H_{20}NO_2$ (M+H), 234.14939; found, 234.15075.

Melting point: 228-229° C.

(3S,4R,5S)-3-amino-4-methyl-5-methyl-2-oxotetrahydrofuran (3S)-(16) from (3S,4R,5S)-3-N-[(S)-1'-phenylethylamino]-4-methyl-5-methyl-2-oxotetrahydrofuran (3S)-(18). HCl A suspension of (3S,4R,5S)-3-N-[(S)-1'-phenyl ethyl amino]-4-methyl-5-methyl-2-oxotetrahydrofuran hydrochloride (1.20 g, 4.46 mmol) and 10% Pd—C (237 mg) in methanol (45 ml) was hydrogenated at room temperature, at atmospheric pressure, overnight. The catalyst was removed by filtration. The solvent was evaporated in order to obtain (3S,4R,5S)-3-amino-4-methyl-5-methyl-2-oxotetrahydrofuran (3S)-(16) (734 mg, 100%).

(2R,3S)-1-cyano-2-methyl-3-tetrahydropyranyloxy-N-[(R)-1'-phenyl-2'-hydroxyethyl]butylamine (19)

(R)-phenylglycinol (115 mg, 0.84 mmol) was added at room temperature to a solution of (2S,3S)-2-methyl-3-tetrahydropyranyloxybutyraldehyde (6) (130 mg, 0.7 mmol) in dichloromethane (6 ml), and the stirring was continued for 2 hours at room temperature. The reaction mixture was cooled to 0° C., and methanol (2 ml) and TMSCN (104 mg, 140 μl, 1.05 mmol) were successively introduced. After stirring at 0° C. for 2 hours and then to room temperature for 22 hours, the reaction mixture was separated in saturated $NaHCO_3$ and in ether. The aqueous phase was extracted with ether, the ether extracts were washed with brine, they were dried and filtered on a short disk of Celite and $Na_2SO_4$ and then evaporated. Flash chromatography on a silica gel column with, as eluent, a heptane/EtOAc=3:1 then 2:1 mixture produced a mixture of (1R,2R,3S)-1-cyano-2-methyl-3-tetrahydropyranyloxy-N-[(R)-1'-phenyl-2'-hydroxyethyl]butylamine (1R)-(19) and (1S,2R,3S)-1-cyano-2-methyl-3-tetrahydropyranyloxy-N-[(R)-1'-phenyl-2'-hydroxyethyl]butylamine (1S)-(19) (225 mg in total, 97%): IR ($CHCl_3$) 3630, 3442, 3347, 3012, 2947, 2856, 1493, 1455, 1385, 1356, 1231, 1173 $cm^{-1}$; $^1H$ NMR (250 MHz, $CDCl_3$) δ 7.37 to 7.27 (m, 5H); 4.72 to 4.39 (m, 1H); 4.14 to 3.39 (m, 7H); 2.30 (broad s, 2H, OH+NH); 2.05 to 1.20 (m, 7H); [1.17 (d, J=6.3 Hz), 1.08 (d, J=7.7 Hz), 1.05. (d, J=7.0 Hz), 6H]; $^{13}C$ NMR (62.5 MHz, $CDCl_3$) δ 140.6; 140.0; 138.7; 138.4; 128.6; 128.0; 127.8; 127.7; 127.3; 120.4; 119.8; 119.6; 119.2; 101.0; 100.1; 97.5; 95.6; 78.9; 76.3; 71.4; 71.2; 67.1; 66.9; 66.0; 65.6; 65.5; 63.2; 63.0; 62.8; 62.7; 53.0; 50.5; 50.1; 49.9; 42.7; 42.5; 42.3; 31.0; 30.8; 30.6; 25.2; 25.0; 21.6; 20.0; 19.6; 19.4; 18.3; 17.0; 16.1; 14.0; 12.7; 12.0; 11.7. MS (CI) m/z 333 $[M+H]^+$. HRMS: calculated for $C_{19}H_{29}N_2O_3$ (M+H), 333.21780; found, 333.21668.

(3S,4R,5S)-3-N-[(R)-1'-phenyl-2'-hydroxyethylamino]-4-methyl-5-methyl-2-oxotetrahydrofuran (3S)-(20) and (3R,4R,5S)-3-N-[(R)-1'-phenyl-2'-hydroxyethylamino]-4-methyl-5-methyl-2-oxotetrahydrofuran (3R)-(20)

A solution of (2R,3S)-1-cyano-2-methyl-3-tetrahydropyranyloxy-N-[(R)-1'-phenyl-2'-hydroxyethyl]butylamine (168 mg, 0.51 mmol) in 6N HCl (10 ml) was refluxed for 6 hours. The reaction mixture was washed with dichloromethane, it was basified with saturated aqueous NaHCO$_3$ and it was extracted with EtOAc. The EtOAc extracts were washed with brine, they were dried and evaporated. Preparative chromatography on a thin layer of silica gel (heptane/EtOAc=1:3) produced (3S,4R,5S)-3-N-[(R)-1'-phenyl-2'-hydroxyethylamino]-4-methyl-5-methyl-2-oxotetrahydrofuran (3S)-(20) (62 mg, 49%) and (3R,4R,5S)-3-N-[(R)-1'-phenyl-2'-hydroxyethylamino]-4-methyl-5-methyl-2-oxotetrahydrofuran (3R)-(20) (32 mg, 25%) [(3S)/(3R)=2:1].

(3S,4R,5S)-3-N-[(R)-1'-phenyl-2'-hydroxyethylamino]-4-methyl-5-methyl-2-oxotetrahydrofuran (3S)-(20) $[\alpha]_D$=−112° (c 1.4, CHCl$_3$); IR (CHCl$_3$) 3596, 3463, 3029, 3014, 2981, 2935, 2877, 1767, 1654, 1493, 1455, 1384, 1356, 1225, 1216, 1176 cm$^{-1}$; $^1$H NMR (250 MHz, CDCl$_3$) δ 7.40 to 7.27 (m, 5H); 4.33 to 4.24 (m, 2H), 3.78 (dd, J=11.1, 4.1 Hz, 1H); 3.59 (dd, J=11.1; 8.8 Hz, 1H); 3.44 (d, J=7.4 Hz, 1H); 2.37 (broad s, 2H, OH+NH); 2.10 to 1.97 (m, 1H); 1.31 (d, J=6.4 Hz, 3H); 1.06 (d, J=7.1 Hz, 3H); $^{13}$C NMR (50 MHz, CDCl$_3$) δ 177.8; 140.1; 128.5; 127.7; 81.4; 67.3; 63.3; 57.1; 40.7; 19.4; 12.3; MS (CI) m/z 250 [M+H]$^+$. HRMS: calculated for C$_{14}$H$_{20}$NO$_3$ (M+H), 250.14431; found, 250.14316.

Enzymatic resolution of (3SR,4R,5S)-3-N-benzylamino-4-methyl-5-methyl-2-oxotetrahydrofuran (3RS)-(11)

(2R,3R,4S)-N-benzyl-4-hydroxyisoleucine was obtained by means of a diastereoselective enzymatic hydrolysis of the lactone (11). This reaction was catalyzed either by a crude enzymatic preparation or with the aid of live microbial cells. In a typical experiment, the lactone (11) was dissolved in a phosphate buffer (40 mM, pH 7.4) and it was stirred in a rotary stirrer at 27° C. The samples were analyzed by HPLC (FIG. 2, at 00 hours, A and B corresponding to (3R)-(11) and (3S)-(11), respectively). As is indicated in FIG. 3, (3R)-(11) was gradually hydrolyzed, while (3S)-(11) remained intact. The latter was extracted with ethyl acetate and it was subjected to another (nonstereo-specific) enzymatic hydrolysis in order to obtain (2R,3R,4S)-N-benzyl-4-hydroxyisoleucine. Catalytic hydrogenolysis of this N-protected amino acid gave (1).

Synthesis of (1) from (17)

a) Synthesis of (3S,4R,5S)-3-N-[(S)-1'-phenylethylamino]-4-methyl-5-methyl-2-oxotetrahydrofuran (3S)-(18) and (3R,4R,5S)-3-N-[(S)-1'-phenylethylamino]-4-methyl-5-methyl-2-oxotetrahydrofuran (3R)-(18) from (17)

A solution of a mixture of (1R,2R,3S) and of (1S,2R,3S)-1-cyano-2-methyl-3-pyranyloxy-N-[(S)-1'-phenylethyl]butylamine (1.73 g, 5.47 mmol), (1R)-17 and (1S)-17, respectively, in 6N HCl (110 ml) was refluxed for 6 hours. The reaction mixture was washed 3 times with EtOAc/heptane (1:1). The aqueous phase was evaporated to give the mixture of (3S,4R,5S)-3-N-[(S)-1'-phenylethylamino]-4-methyl-5-methyl-2-oxotetrahydrofuran (3S)-(18) and (3R,4R,5S)-3-N-[(S)-1'-phenylethylamino]-4-methyl-5-methyl-2-oxotetrahydrofuran (3R)-(18) ((2S)/(2R)=4.5:1). The residue thus obtained was directly used in the next step in the form of a HCl salt.

Synthesis of (1) from (18)

The mixture of (3S) and (3R)-18 prepared above was dissolved in water (110 ml) and then treated with LiOH.H$_2$O (459 mg, 10.94 mmol) for 24 hours at room temperature. TFA (2.2 ml) was added to the reaction mixture and the solvent was immediately evaporated under vacuum at 40-45° C. The residue was dissolved in water and extracted with EtOAc. The aqueous phase was hydrogenated in the presence of 10% Pd—C overnight at room temperature and at atmospheric pressure. The catalyst was removed by filtration. The solvent was evaporated and the residue dissolved in water and passed through a column of ion-exchange resin Dowex 50WX8 (H+ form). The column was meticulously washed with water and the amino acid was eluted with 2M NH$_4$OH in order to obtain compound (1) (423 mg, 59% for three steps). Melting point=224° C.; $[\alpha]_D^{20}$=+31.5° (c 1, H$_2$O); $^1$H NMR (250 MHz, D$_2$O) δ 3.88 (d, J=4.4 Hz, 1H); 3.78 (m, 1H); 1.91 (m, 1H); 1.23 (d, J=6.5 Hz, 3H); 0.95 (d, J=7 Hz, 3H); $^{13}$C NMR (50 MHz, D$_2$O) δ 174.2; 70.4; 57.5; 41.9; 21.3; MS (ES) m/z 148 [M+H]$^+$. Microanalysis: calculated for C$_6$H$_{13}$NO$_3$, C, 48.97; H, 8.90; N, 9.52; found, C, 49.04; H, 8.83; N, 9.60.

(2R)-N-(1'-Phenylethyl)-1

$^1$H NMR (250 MHz, D$_2$O) δ 7.44 to 7.37 (m, 5H); 4.10 (q, J=6.8 Hz, 1H); 3.85 (quintet, J=6.2 Hz, 1H); 3.72 (d, J=3.2 Hz, 1H); 1.95 (m, 1H); 1.52 (d, J=6.8 Hz, 3H); 1.25 (d, J=6.4 Hz, 3H); 0.91(d, J=7.3 Hz, 3h); $^{13}$C NMR (50 MHz, D$_2$O+ CD$_3$OD) δ 172.9; 137.5; 130.6; 128.7; 71.3; 63.4; 59.3; 40.7; 22.1; 18.5; 13.7.

(2S)-N-(1'-Phenylethyl)-1

Melting point=. 155-157° C. (decomposition) $[\alpha]_D$=−25° (c 1.0, H$_2$O); $^1$H NMR (250 MHz, D$_2$O) δ 7.42 to 7.32 (m, 5H); 4.23 (q, J=6.8 Hz, 1H); 3.48 (m, 1H); 3.34 (d, J=5.8 Hz, 1H); 1.64 (m, 1H); 1.60 (d, J=6.8 Hz, 3H); 1.00 (d, J=6.2 Hz, 3H); 0.76 (d, J=6.9 Hz, 3H); $^{13}$C NMR (50 MHz, D$_2$O) δ 172.0; 135.1; 129.5; 129.2; 127.5; 70.6; 63.4; 58.3; 40.7; 20.5; 18.9; 11.9.

The invention claimed is:

1. A method for synthesizing compounds of the following general formula (2S)-1:

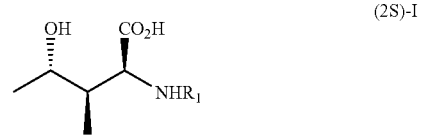

(2S)-I wherein the group R$_1$ represents a hydrogen atom, a benzyl, (S)-(+)-p-toluenesulfino, (S)-1-phenylethyl or (S)-1-phenyl-2-hydroxyethyl group or a group of formula —COOR$_2$ wherein group R$_2$ represents an aryl group, an aralkyl group or a C$_1$-C$_6$ alkyl group, comprising the steps of:

a) diastereo- and enantioselective reduction of the compound of the following formula 2:

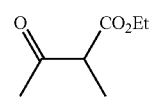

2 using the microorganism *Geotrichum candidum* in order to obtain the compound of the following formula 3:

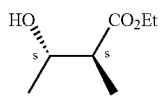

with an enantiomeric excess of at least about 85% and a diastereomeric excess of at least about 90%;

b) protecting the OH group of the alcohol of formula 3 with a group Y;
c) reducing the group —COOEt to an alcohol;
d) oxidizing the unprotected OH group obtained in c) to obtain the aldehyde of the following general formula II:

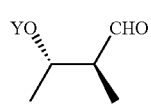

wherein group Y represents a benzyl, t-butyl or tetrahydropyran group, and wherein said method of synthesis is further comprised of either one of two routes of synthesis identified as method A and method B, wherein method A comprises the steps of:

$e_1$) treating the compound of general formula II with a sulfinamide having the configuration (S)(+) in order to obtain the compound of the following general formula IV:

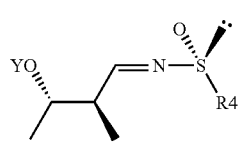

wherein group Y represents a benzyl, t-butyl or tetrahydropyran group and group R4 represents a $C_1$-$C_6$ alkyl, aryl or aralkyl group;

$f_1$) treating the compound of general formula IV with ethylisopropyloxyaluminim cyanide (EtAl(OiPr)CN) in order to obtain the aminonitrile of the following general formula V:

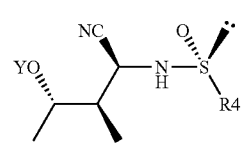

wherein group Y represents a benzyl, t-butyl or tetrahydropyran group and group R4 represents a $C_1$-$C_6$ alkyl, aryl or aralkyl group;

$g_1$) treating the aminonitrile of general formula V with an inorganic acid in order to obtain the salt of the lactone of the following formula 9:

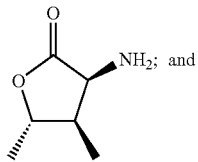

$h_1$) alkaline hydrolysis of the salt of the lactone of formula 9 in order to obtain the compound of general formula (2S)-I wherein group $R_1$ represents a hydrogen atom, and wherein method B comprises the steps of:

$e_2$) treating the compound of general formula II in order to obtain the aminonitrile of the following general formula III:

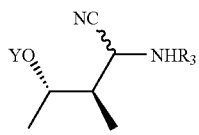

wherein group Y represents a benzyl, t-butyl or tetrahydropyran group and group $R_3$ represents a benzyl, (S)-(+)-p-toluenesulfino, (S)-1-phenylethyl or (S)-1-phenyl-2-hydroxyethyl group;

$f_2$) treating with an acid of the aminonitrile of general formula III in order to obtain the lactone of the following general formula VI:

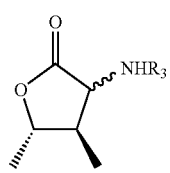

wherein $R_3$ represents hydrogen atom or a group protecting the amine group, however if $R_3$ represents a benzyl, (S)-(+)-p-toluenesulfino, (S)-1-phenylethyl or (S)-1-phenyl-2-hydroxyethyl group or if $R_1$ does not represent a hydrogen atom and $R_3$ represents a hydrogen atom, step $f_2$ is followed by an additional step $f_{2.1}$) which consists of treating the lactone of general formula VI in order to obtain the lactone of the following general formula VII:

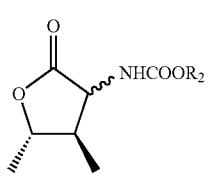

and wherein group $R_2$ represents an aryl group, an aralkyl group or an $C_1$-$C_6$ alkyl group; and g₂) diastereoselective hydrolysis of the lactone of general formula VI or VII in order to obtain the compound of general formula (2S)-I.

2. The method as claimed in claim 1, wherein group R₃ represents the group protecting the amine group and the diastereoselective hydrolysis consists of:

crystallization, from an alcohol, of the lactone of general formula VI in an organic solvent so as to obtain the salt of the compound of formula (3S)-VIII:

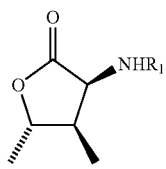

(3S)-VIII (c1) wherein group R₁ represents a benzyl, (S)-(+)-p-toluenesulfino, (S)-1-phenylethyl or (S)-1-phenyl-2-hydroxyethyl group;

catalytic hydrogenolysis of the salt of the compound of formula (3S)-VIII wherein group R₁ represents a benzyl, (S)-(+)-p-toluenesulfino, (S)-1-phenylethyl or (S)-1-phenyl-2-hydroxyethyl group so as to obtain the salt of the lactone of formula 9; and alkaline hydrolysis of the salt of the lactone of formula 9 in order to obtain the compound of general formula (2S)-I and wherein group R₁ represents a hydrogen atom.

3. The method as claimed in claim 1, wherein group R₃ represents a benzyl, (S)-(+)-p-toluenesulfino, (S)-1-phenylethyl or (S)-1-phenyl-2-hydroxyethyl group and group R₁ represents a benzyl, (S)-(+)-p-toluenesulfino, (S)-1-phenylethyl or (S)-1-phenyl-2-hydroxyethyl group or a group of formula —COOR₂ wherein group R₂ represents an aryl group, an aralkyl group or a C₁-C₆ alkyl group, and further comprising the step h₂) of catalytic hydrogenolysis of the compound of formula (2S)-I wherein group R₁ represents a group protecting the amine group or a group of formula —COOR₂ wherein group R₂ represents an aryl group, an aralkyl group or a C₁-C₆ alkyl group in order to obtain the compound of general formula (2S)-I wherein group R₁ represents a hydrogen atom.

\* \* \* \* \*